US011464581B2

(12) United States Patent
Calloway

(10) Patent No.: US 11,464,581 B2
(45) Date of Patent: Oct. 11, 2022

(54) POSE MEASUREMENT CHAINING FOR EXTENDED REALITY SURGICAL NAVIGATION IN VISIBLE AND NEAR INFRARED SPECTRUMS

(71) Applicant: GLOBUS MEDICAL, INC., Audubon, PA (US)

(72) Inventor: Thomas Calloway, Pelham, NH (US)

(73) Assignee: Globus Medical, Inc., Audubon, PA (US)

(*) Notice: Subject to any disclaimer, the term of this patent is extended or adjusted under 35 U.S.C. 154(b) by 362 days.

(21) Appl. No.: 16/774,799

(22) Filed: Jan. 28, 2020

(65) Prior Publication Data

US 2021/0228281 A1 Jul. 29, 2021

(51) Int. Cl.

*A61B 34/20* (2016.01)
*G02B 27/01* (2006.01)
*G06T 19/00* (2011.01)

(52) U.S. Cl.

CPC .......... *A61B 34/20* (2016.02); *G02B 27/0172* (2013.01); *G06T 19/006* (2013.01); *A61B 2034/2055* (2016.02)

(58) Field of Classification Search

CPC ......... A61B 34/20; A61B 34/30; A61B 34/25; A61B 2034/107; A61B 2034/2057; A61B 2090/365; A61B 2090/371; A61B 2090/372; A61B 2090/376; A61B 2090/3762; A61B 2090/3983; A61B 2090/502; A61B 34/10; A61B 90/361; A61B 90/37; A61B 2034/108; A61B 2034/2065; A61B 2090/373; G02B 27/0172; G06T 19/006; G06T 7/20; G06T 7/292; G06T 7/70

See application file for complete search history.

(56) References Cited

U.S. PATENT DOCUMENTS

| | | | |
|---|---|---|---|
| 4,150,293 | A | 4/1979 | Franke |
| 4,722,056 | A | 1/1988 | Roberts et al. |
| 5,246,010 | A | 9/1993 | Gazzara et al. |

(Continued)

FOREIGN PATENT DOCUMENTS

| | | | |
|---|---|---|---|
| JP | 2017-514608 | A | 6/2017 |
| WO | 2017066373 | A1 | 4/2017 |
| WO | 2017114834 | A1 | 7/2017 |

*Primary Examiner* — Jeffery A Brier

(57) ABSTRACT

A surgical system includes a camera tracking system that determines a first pose transform between a first object coordinate system and the first tracking camera coordinate system based on first object tracking information from the first tracking camera which indicates pose of the first object. The camera tracking system determines a second pose transform between the first object coordinate system and the second tracking camera coordinate system based on first object tracking information from the second tracking camera indicating pose of the first object, and determines a third pose transform between a second object coordinate system and the second tracking camera coordinate system based on second object tracking information from the second tracking camera indicating pose of the second object. The camera tracking system determines a fourth pose transform between the second object coordinate system and the first tracking camera coordinate system.

20 Claims, 19 Drawing Sheets

(E)
1200
(a)
(c)
(N2)
(b)
(d)
1210
(N3)
1900
(R)

(56) References Cited

U.S. PATENT DOCUMENTS 5,526,812 A 6/1996 Dumoulin et al.
5,598,453 A 1/1997 Baba et al.
5,740,802 A 4/1998 Nafis et al.
5,772,594 A 6/1998 Barrick
5,961,456 A 10/1999 Gildenberg
5,987,960 A 11/1999 Messner et al.
6,006,126 A 12/1999 Cosman
6,031,888 A 2/2000 Ivan et al.
6,144,875 A 11/2000 Schweikard et al.
6,203,196 B1 3/2001 Meyer et al.
6,226,548 B1 5/2001 Foley et al.
6,301,495 B1 10/2001 Gueziec et al.
6,306,126 B1 10/2001 Montezuma
6,314,311 B1 11/2001 Williams et al.
6,320,929 B1 11/2001 Von Der Haar
6,349,001 B1 2/2002 Spitzer
6,477,400 B1 11/2002 Barrick
6,484,049 B1 11/2002 Seeley et al.
6,487,267 B1 11/2002 Wolter
6,490,475 B1 12/2002 Seeley et al.
6,501,981 B1 12/2002 Schweikard et al.
6,503,195 B1 1/2003 Keller et al.
6,535,756 B1 3/2003 Simon et al.
6,544,176 B2 4/2003 Mikus et al.
6,614,453 B1 9/2003 Suri et al.
6,614,871 B1 9/2003 Kobiki et al.
6,619,840 B2 9/2003 Rasche et al.
6,666,579 B2 12/2003 Jensen
6,669,635 B2 12/2003 Kessman et al.
6,725,080 B2 4/2004 Melkent et al.
6,757,068 B2 6/2004 Foxlin
6,782,287 B2 8/2004 Grzeszczuk et al.
6,856,324 B2 2/2005 Sauer et al.
6,856,826 B2 2/2005 Seeley et al.
6,856,827 B2 2/2005 Seeley et al.
6,867,753 B2 3/2005 Chinthammit et al.
6,919,867 B2 7/2005 Sauer
6,920,347 B2 7/2005 Simon et al.
6,922,632 B2 7/2005 Foxlin
6,947,786 B2 9/2005 Simon et al.
6,988,009 B2 1/2006 Grimm et al.
6,996,487 B2 2/2006 Jutras et al.
7,016,457 B1 3/2006 Senzig et al.
7,043,961 B2 5/2006 Pandey et al.
7,050,845 B2 5/2006 Vilsmeier
7,062,006 B1 6/2006 Pelc et al.
7,063,705 B2 6/2006 Young et al.
7,072,707 B2 7/2006 Galloway, Jr. et al.
7,099,428 B2 8/2006 Clinthorne et al.
7,108,421 B2 9/2006 Gregerson et al.
7,130,676 B2 10/2006 Barrick
7,139,418 B2 11/2006 Abovitz et al.
7,176,936 B2 2/2007 Sauer et al.
7,194,120 B2 3/2007 Wicker et al.
7,197,107 B2 3/2007 Arai et al.
7,231,014 B2 6/2007 Levy
7,231,063 B2 6/2007 Naimark et al.
7,301,648 B2 11/2007 Foxlin
7,313,430 B2 12/2007 Urquhart et al.
7,318,805 B2 1/2008 Schweikard et al.
7,324,623 B2 1/2008 Heuscher et al.
7,327,865 B2 2/2008 Fu et al.
7,460,637 B2 12/2008 Clinthorne et al.
7,480,402 B2 1/2009 Bar-Zohar et al.
7,493,153 B2 2/2009 Ahmed et al.
7,505,617 B2 3/2009 Fu et al.
7,542,791 B2 6/2009 Mire et al.
7,570,791 B2 8/2009 Frank et al.
7,599,730 B2 10/2009 Hunter et al.
7,605,826 B2 10/2009 Sauer
7,606,613 B2 10/2009 Simon et al.
7,623,902 B2 11/2009 Pacheco
7,643,862 B2 1/2010 Schoenefeld
7,661,881 B2 2/2010 Gregerson et al.
7,683,331 B2 3/2010 Chang
7,683,332 B2 3/2010 Chang
7,702,379 B2 4/2010 Avinash et al.
7,702,477 B2 4/2010 Tuemmler et al.
7,711,083 B2 5/2010 Heigl et al.
7,725,253 B2 5/2010 Foxlin
7,726,171 B2 6/2010 Langlotz et al.
7,760,849 B2 7/2010 Zhang
7,774,044 B2 8/2010 Sauer et al.
7,796,728 B2 9/2010 Bergfjord
7,813,838 B2 10/2010 Sommer
7,831,294 B2 11/2010 Viswanathan
7,835,778 B2 11/2010 Foley et al.
7,835,784 B2 11/2010 Mire et al.
7,840,256 B2 11/2010 Lakin et al.
7,844,320 B2 11/2010 Shahidi
7,853,305 B2 12/2010 Simon et al.
7,853,313 B2 12/2010 Thompson
7,900,524 B2 3/2011 Calloway et al.
7,940,999 B2 5/2011 Liao et al.
7,945,012 B2 5/2011 Ye et al.
7,945,021 B2 5/2011 Shapiro et al.
7,953,470 B2 5/2011 Vetter et al.
7,987,001 B2 7/2011 Teichman et al.
8,019,045 B2 9/2011 Kato
8,021,310 B2 9/2011 Sanborn et al.
8,052,688 B2 11/2011 Wolf, II
8,086,299 B2 12/2011 Adler et al.
8,098,914 B2 1/2012 Liao et al.
8,100,950 B2 1/2012 St. Clair et al.
8,106,905 B2 1/2012 Markowitz et al.
8,116,430 B1 2/2012 Shapiro et al.
8,121,249 B2 2/2012 Wang et al.
8,123,675 B2 2/2012 Funda et al.
8,150,494 B2 4/2012 Simon et al.
8,208,708 B2 6/2012 Homan et al.
8,224,024 B2 7/2012 Foxlin et al.
8,228,368 B2 7/2012 Zhao et al.
8,311,611 B2 11/2012 Csavoy et al.
8,314,815 B2 11/2012 Navab et al.
8,325,873 B2 12/2012 Helm et al.
8,335,557 B2 12/2012 Maschke
8,358,818 B2 1/2013 Miga et al.
8,374,673 B2 2/2013 Adcox et al.
8,379,791 B2 2/2013 Forthmann et al.
8,386,019 B2 2/2013 Camus et al.
8,394,099 B2 3/2013 Patwardhan
8,427,527 B2 4/2013 Visser et al.
8,462,911 B2 6/2013 Vesel et al.
8,504,136 B1 8/2013 Sun et al.
8,509,503 B2 8/2013 Nahum et al.
8,526,700 B2 9/2013 Isaacs
8,532,741 B2 9/2013 Heruth et al.
8,541,970 B2 9/2013 Nowlin et al.
8,560,118 B2 10/2013 Green et al.
8,597,198 B2 12/2013 Sanborn et al.
8,611,985 B2 12/2013 Lavallee et al.
8,630,389 B2 1/2014 Kato
8,634,897 B2 1/2014 Simon et al.
8,660,635 B2 2/2014 Simon et al.
8,672,836 B2 3/2014 Higgins et al.
8,678,647 B2 3/2014 Gregerson et al.
8,696,458 B2 4/2014 Foxlin et al.
8,700,123 B2 4/2014 Okamura et al.
8,706,185 B2 4/2014 Foley et al.
8,727,618 B2 5/2014 Maschke et al.
8,738,115 B2 5/2014 Amberg et al.
8,740,882 B2 6/2014 Jun et al.
8,774,363 B2 7/2014 Van Den Houten et al.
8,781,186 B2 7/2014 Clements et al.
8,781,630 B2 7/2014 Banks et al.
8,784,443 B2 7/2014 Tripathi
8,787,520 B2 7/2014 Baba
8,792,704 B2 7/2014 Isaacs
8,798,231 B2 8/2014 Notohara et al.
8,812,077 B2 8/2014 Dempsey
8,814,793 B2 8/2014 Brabrand
8,818,105 B2 8/2014 Myronenko et al.
8,821,511 B2 9/2014 Von Jako et al.
8,842,893 B2 9/2014 Teichman et al.

(56) References Cited

U.S. PATENT DOCUMENTS 8,867,703 B2 10/2014 Shapiro et al.
8,878,900 B2 11/2014 Yang et al.
8,888,821 B2 11/2014 Rezach et al.
8,891,847 B2 11/2014 Helm et al.
8,938,283 B2 1/2015 Zentgraf et al.
8,938,301 B2 1/2015 Hagedorn
8,945,140 B2 2/2015 Hubschman et al.
8,948,935 B1 2/2015 Peeters et al.
8,964,934 B2 2/2015 Ein-Gal
8,992,580 B2 3/2015 Bar et al.
8,996,169 B2 3/2015 Lightcap et al.
9,001,963 B2 4/2015 Sowards-Emmerd et al.
9,002,076 B2 4/2015 Khadem et al.
9,044,190 B2 6/2015 Rubner et al.
9,095,252 B2 8/2015 Popovic
9,105,207 B2 8/2015 Leung
9,107,683 B2 8/2015 Hourtash et al.
9,119,670 B2 9/2015 Yang et al.
9,123,155 B2 9/2015 Cunningham et al.
9,125,556 B2 9/2015 Zehavi et al.
9,131,986 B2 9/2015 Greer et al.
9,215,968 B2 12/2015 Schostek et al.
9,232,982 B2 1/2016 Soler et al.
9,265,468 B2 2/2016 Rai et al.
9,289,267 B2 3/2016 Sauer et al.
9,295,435 B2 3/2016 Florent et al.
9,308,050 B2 4/2016 Kostrzewski et al.
9,333,361 B2 5/2016 Li et al.
9,380,984 B2 7/2016 Li et al.
9,393,039 B2 7/2016 Lechner et al.
9,398,886 B2 7/2016 Gregerson et al.
9,398,890 B2 7/2016 Dong et al.
9,414,859 B2 8/2016 Ballard et al.
9,420,975 B2 8/2016 Gutfleisch et al.
9,436,993 B1 9/2016 Stolka et al.
9,439,556 B2 9/2016 Pandya et al.
9,492,235 B2 11/2016 Hourtash et al.
9,492,241 B2 11/2016 Jaskowicz et al.
9,498,132 B2 11/2016 Maier-Hein et al.
9,538,962 B1 1/2017 Hannaford et al.
9,547,940 B1 1/2017 Sun et al.
9,554,866 B2 1/2017 Cunningham et al.
9,563,266 B2 2/2017 Banerjee et al.
9,576,106 B2 2/2017 Ahmad
9,592,096 B2 3/2017 Maillet et al.
9,626,805 B2 4/2017 Lampotang et al.
9,645,379 B2 5/2017 Ren et al.
9,681,925 B2 6/2017 Azar et al.
9,707,400 B2 7/2017 Grenz et al.
9,750,465 B2 9/2017 Engel et al.
9,757,203 B2 9/2017 Hourtash et al.
9,767,608 B2 9/2017 Lee et al.
9,773,312 B2 9/2017 Lee
9,788,756 B2 10/2017 Demmer
9,795,282 B2 10/2017 Sholev et al.
9,795,354 B2 10/2017 Menegaz et al.
9,814,535 B2 11/2017 Bar et al.
9,820,783 B2 11/2017 Donner et al.
9,833,265 B2 11/2017 Donner et al.
9,833,254 B1 12/2017 Barral et al.
9,835,862 B1 12/2017 Zhou et al.
9,839,365 B1 12/2017 Homyk et al.
9,848,922 B2 12/2017 Tohmeh et al.
9,855,103 B2 1/2018 Tsekos et al.
9,892,564 B1 2/2018 Cvetko et al.
9,895,063 B1 2/2018 Hannaford et al.
9,898,662 B2 2/2018 Tsuda et al.
9,911,187 B2 3/2018 Steinle et al.
9,925,011 B2 3/2018 Gombert et al.
9,925,013 B2 3/2018 Dell et al.
9,928,629 B2 3/2018 Benishti et al.
9,931,025 B1 4/2018 Graetzel et al.
9,931,040 B2 4/2018 Homyk et al.
9,949,637 B1 4/2018 Wong et al.
9,970,955 B1 5/2018 Homyk et al.
9,980,698 B2 5/2018 Bakker et al.
10,010,373 B2 7/2018 Canfield et al.
10,010,379 B1 7/2018 Gibby et al.
10,013,808 B2 7/2018 Jones et al.
10,016,243 B2 7/2018 Esterberg
10,034,717 B2 7/2018 Miller et al.
10,052,170 B2 8/2018 Saget et al.
10,073,515 B2 9/2018 Awdeh
10,092,164 B2 10/2018 Sholev et al.
10,092,237 B2 10/2018 Wong et al.
10,092,361 B2 10/2018 Ferro et al.
10,105,187 B2 10/2018 Corndorf et al.
10,152,789 B2 12/2018 Carnes et al.
10,152,796 B2 12/2018 Guo et al.
10,154,239 B2 12/2018 Casas
10,163,252 B2 12/2018 Yun et al.
10,166,019 B2 1/2019 Nawana et al.
10,176,642 B2 1/2019 Tran et al.
10,191,615 B2 1/2019 Helm et al.
10,194,990 B2 2/2019 Amanatullah et al.
10,195,076 B2 2/2019 Fateh
10,197,803 B2 2/2019 Badiali et al.
10,197,816 B2 2/2019 Waisman et al.
10,226,298 B2 3/2019 Ourselin et al.
10,231,784 B2 3/2019 Hettrick et al.
10,235,737 B2 3/2019 Cheatham, III et al.
10,242,292 B2 3/2019 Zisimopoulos et al.
10,251,714 B2 4/2019 Carnes et al.
10,258,426 B2 4/2019 Silva et al.
10,265,138 B2 4/2019 Choudhry et al.
10,275,927 B2 4/2019 Kuhn et al.
10,278,726 B2 5/2019 Barth et al.
10,285,765 B2 5/2019 Sachs et al.
10,292,780 B2 5/2019 Park
10,360,730 B2 7/2019 Hasegwa
10,366,489 B2 7/2019 Boettger et al.
10,376,318 B2 8/2019 Tsusaka et al.
10,379,048 B2 8/2019 Wang et al.
10,383,654 B2 8/2019 Yilmaz et al.
10,390,780 B2 8/2019 Han et al.
10,390,890 B2 8/2019 Jagga
10,390,891 B2 8/2019 Govari et al.
10,398,514 B2 9/2019 Ryan et al.
10,405,927 B1 9/2019 Lang
10,412,377 B2 9/2019 Forthmann et al.
10,413,363 B2 9/2019 Fahim et al.
10,426,339 B2 10/2019 Papac
10,426,345 B2 10/2019 Shekhar et al.
10,426,554 B2 10/2019 Siewerdsen et al.
10,431,008 B2 10/2019 Djajadiningrat et al.
10,432,913 B2 10/2019 Shokri et al.
10,433,915 B2 10/2019 Isaacs et al.
10,448,003 B2 10/2019 Gafenberg
2001/0036302 A1 11/2001 Miller
2003/0179308 A1 9/2003 Zamorano et al.
2003/0210812 A1 11/2003 Khamene et al.
2004/0076259 A1 4/2004 Jensen et al.
2004/0106916 A1 6/2004 Quaid et al.
2004/0254454 A1 12/2004 Kockro
2005/0054910 A1 3/2005 Tremblay et al.
2005/0215879 A1 9/2005 Chuanggui
2006/0176242 A1 8/2006 Jaramaz et al.
2006/0184396 A1 8/2006 Dennis et al.
2006/0291612 A1 12/2006 Nishide et al.
2006/0293557 A1 12/2006 Chuanggui et al.
2007/0021738 A1 1/2007 Hasset et al.
2007/0038059 A1 2/2007 Sheffer et al.
2007/0073133 A1 3/2007 Schoenefeld
2007/0167702 A1 7/2007 Hasser et al.
2007/0236514 A1 10/2007 Agusanto et al.
2007/0238981 A1 10/2007 Zhu et al.
2007/0248261 A1 10/2007 Zhou et al.
2008/0004523 A1 1/2008 Jensen
2008/0013809 A1 1/2008 Zhu et al.
2008/0082109 A1 4/2008 Moll et al.
2008/0108991 A1 5/2008 Von Jako
2008/0123910 A1 5/2008 Zhu
2008/0144906 A1 6/2008 Allred et al.
2008/0161680 A1 7/2008 Von Jako et al.

(56) References Cited

U.S. PATENT DOCUMENTS

2008/0183068 A1 7/2008 Carls et al.
2008/0183074 A1 7/2008 Carls et al.
2008/0183188 A1 7/2008 Carls et al.
2008/0235052 A1 9/2008 Node-Langlois et al.
2008/0243142 A1 10/2008 Gildenberg
2008/0269596 A1 10/2008 Revie et al.
2008/0287781 A1 11/2008 Revie et al.
2008/0300477 A1 12/2008 Lloyd et al.
2008/0302950 A1 12/2008 Park et al.
2008/0306490 A1 12/2008 Lakin et al.
2008/0319311 A1 12/2008 Hamadeh
2009/0185655 A1 7/2009 Koken et al.
2009/0198121 A1 8/2009 Hoheisel
2010/0022874 A1 1/2010 Wang et al.
2010/0039506 A1 2/2010 Sarvestani et al.
2010/0125286 A1 5/2010 Wang et al.
2010/0210902 A1 8/2010 Navab et al.
2010/0228117 A1 9/2010 Hartmann
2010/0274120 A1 10/2010 Heuscher
2011/0098553 A1 4/2011 Robbins et al.
2011/0282189 A1 11/2011 Graumann
2011/0286573 A1 11/2011 Schretter et al.
2011/0306986 A1 12/2011 Lee et al.
2012/0035507 A1 2/2012 George et al.
2012/0051498 A1 3/2012 Koishi
2012/0059378 A1 3/2012 Farrell
2012/0143084 A1 6/2012 Shoham
2012/0203067 A1 8/2012 Higgins et al.
2012/0226145 A1 9/2012 Chang et al.
2012/0235909 A1 9/2012 Birkenbach et al.
2012/0294498 A1 11/2012 Popovic
2012/0302875 A1 11/2012 Kohring
2013/0016889 A1 1/2013 Myronenko et al.
2013/0060146 A1 3/2013 Yang et al.
2013/0094742 A1 4/2013 Feilkas
2013/0113791 A1 5/2013 Isaacs et al.
2013/0165937 A1 6/2013 Patwardhan
2013/0211232 A1 8/2013 Murphy et al.
2013/0267838 A1 10/2013 Fronk et al.
2013/0274596 A1 10/2013 Azizian et al.
2013/0281821 A1 10/2013 Liu et al.
2013/0307955 A1 11/2013 Deitz et al.
2013/0342578 A1 12/2013 Isaacs
2013/0345757 A1 12/2013 Stad
2014/0022283 A1 1/2014 Chan et al.
2014/0044333 A1 2/2014 Barth, Jr. et al.
2014/0046132 A1 2/2014 Hoeg et al.
2014/0049629 A1 2/2014 Siewerdsen et al.
2014/0080086 A1 3/2014 Chen
2014/0096369 A1 4/2014 Matsumoto et al.
2014/0121676 A1 5/2014 Kostrzewski et al.
2014/0135796 A1 5/2014 Simon et al.
2014/0139405 A1 5/2014 Ribble et al.
2014/0206994 A1 7/2014 Jain et al.
2014/0130810 A1 8/2014 Azizian et al.
2014/0221819 A1 8/2014 Sarment
2014/0234804 A1 8/2014 Huang et al.
2014/0347353 A1 11/2014 Popovic et al.
2014/0371577 A1 12/2014 Maillet et al.
2015/0031990 A1 1/2015 Boctor et al.
2015/0039034 A1 2/2015 Frankel et al.
2015/0073265 A1 3/2015 Popovic et al.
2015/0084990 A1 3/2015 Laor
2015/0085970 A1 3/2015 Bouhnik et al.
2015/0112126 A1 4/2015 Popovic et al.
2015/0146847 A1 5/2015 Liu
2015/0146946 A1 5/2015 Elhawary et al.
2015/0150524 A1 6/2015 Yorkston et al.
2015/0196261 A1 7/2015 Funk
2015/0201892 A1 7/2015 Hummel et al.
2015/0213633 A1 7/2015 Chang et al.
2015/0230689 A1 8/2015 Blohm et al.
2015/0238276 A1 8/2015 Atarot et al.
2015/0248793 A1 9/2015 Abovitz et al.
2015/0305828 A1 10/2015 Park et al.
2015/0335480 A1 11/2015 Alvarez et al.
2015/0342647 A1 12/2015 Frankel et al.
2015/0366624 A1 12/2015 Kostrzewski et al.
2015/0366628 A1 12/2015 Ingmanson
2016/0005194 A1 1/2016 Schretter et al.
2016/0015469 A1 1/2016 Goshayesh et al.
2016/0015470 A1 1/2016 Border
2016/0018640 A1 1/2016 Haddick et al.
2016/0018641 A1 1/2016 Haddick et al.
2016/0018642 A1 1/2016 Haddick et al.
2016/0019715 A1 1/2016 Haddick et al.
2016/0019716 A1 1/2016 Huang et al.
2016/0019719 A1 1/2016 Osterhout et al.
2016/0021304 A1 1/2016 Osterhout
2016/0022125 A1 1/2016 Nicolau et al.
2016/0086380 A1 3/2016 Vayser et al.
2016/0163105 A1 6/2016 Hong et al.
2016/0166329 A1 6/2016 Langan et al.
2016/0225192 A1 8/2016 Jones et al.
2016/0235480 A1 8/2016 Scholl et al.
2016/0249989 A1 9/2016 Devam et al.
2016/0249990 A1 9/2016 Glozman et al.
2016/0287337 A1 10/2016 Aram et al.
2016/0302871 A1 10/2016 Gregerson et al.
2016/0317119 A1 11/2016 Tahmasebi Maraghoosh et al.
2016/0320322 A1 11/2016 Suzuki
2016/0324580 A1 11/2016 Esterberg
2016/0324598 A1 11/2016 Bothorel et al.
2016/0331335 A1 11/2016 Gregerson et al.
2016/0360117 A1 12/2016 Elefteriu et al.
2017/0035517 A1 2/2017 Geri et al.
2017/0053437 A1 2/2017 Ye et al.
2017/0099479 A1 4/2017 Browd et al.
2017/0119471 A1 5/2017 Winner et al.
2017/0119474 A1 5/2017 Kronman
2017/0135770 A1 5/2017 Scholl et al.
2017/0143284 A1 5/2017 Sehnert et al.
2017/0143426 A1 5/2017 Isaacs et al.
2017/0151034 A1 6/2017 Oda et al.
2017/0156816 A1 6/2017 Ibrahim
2017/0172381 A1 6/2017 Morimoto
2017/0172663 A1 6/2017 Popovic et al.
2017/0181802 A1 6/2017 Sachs et al.
2017/0202624 A1 7/2017 Atarot et al.
2017/0202629 A1 7/2017 Maillet et al.
2017/0202633 A1 7/2017 Liu
2017/0212723 A1 7/2017 Atarot et al.
2017/0215825 A1 8/2017 Johnson et al.
2017/0215826 A1 8/2017 Johnson et al.
2017/0215827 A1 8/2017 Johnson et al.
2017/0224427 A1 8/2017 Lavallee et al.
2017/0231710 A1 8/2017 Scholl et al.
2017/0231714 A1 8/2017 Kosmecki et al.
2017/0251900 A1 9/2017 Hansen et al.
2017/0256095 A1 9/2017 Bani-Hashemi
2017/0258426 A1 9/2017 Risher-Kelly et al.
2017/0273549 A1 9/2017 Nazareth et al.
2017/0273748 A1 9/2017 Hourtash et al.
2017/0296277 A1 10/2017 Hourtash et al.
2017/0296292 A1 10/2017 Mahmood et al.
2017/0315364 A1 11/2017 Masumoto
2017/0322410 A1 11/2017 Watson et al.
2017/0323062 A1 11/2017 Djajadiningrat et al.
2017/0336870 A1 11/2017 Everett et al.
2017/0360493 A1 12/2017 Zucher et al.
2017/0367766 A1 12/2017 Mahfouz
2017/0367771 A1 12/2017 Tako et al.
2018/0021099 A1 1/2018 Warner et al.
2018/0032130 A1 2/2018 Meglan
2018/0042692 A1 2/2018 Kim et al.
2018/0049809 A1 2/2018 Marti et al.
2018/0071032 A1 3/2018 De Almeida Barreto
2018/0078316 A1 3/2018 Schaewe et al.
2018/0082480 A1 3/2018 White et al.
2018/0092698 A1 4/2018 Chopra et al.
2018/0092706 A1 4/2018 Anderson et al.
2018/0116724 A1 5/2018 Gmeiner et al.
2018/0116732 A1 5/2018 Lin et al.
2018/0125586 A1 5/2018 Sela et al.

(56) References Cited

U.S. PATENT DOCUMENTS

2018/0140362 A1 5/2018 Cali et al.
2018/0158201 A1 6/2018 Thompson et al.
2018/0161102 A1 6/2018 Wei et al.
2018/0168730 A1 6/2018 Nazy
2018/0168741 A1 6/2018 Swayze
2018/0168769 A1 6/2018 Wood et al.
2018/0185100 A1 7/2018 Weinstein et al.
2018/0220100 A1 8/2018 Ovchinnikov et al.
2018/0228555 A1 8/2018 Charron et al.
2018/0232925 A1 8/2018 Frakes et al.
2018/0233222 A1 8/2018 Daley et al.
2018/0235739 A1 8/2018 Jahn
2018/0247449 A1 8/2018 Park et al.
2018/0249912 A1 9/2018 Schneider et al.
2018/0256256 A1 9/2018 May et al.
2018/0263698 A1 9/2018 Wang et al.
2018/0263727 A1 9/2018 Pellerito
2018/0289428 A1 10/2018 Lee et al.
2018/0289983 A1 10/2018 Fishman
2018/0299675 A1 10/2018 Benz et al.
2018/0303377 A1 10/2018 West et al.
2018/0303558 A1 10/2018 Thomas
2018/0303667 A1 10/2018 Peyman
2018/0310811 A1 11/2018 Meglan et al.
2018/0310831 A1 11/2018 Cheng et al.
2018/0310875 A1 11/2018 Meglan et al.
2018/0325604 A1 11/2018 Atarot et al.
2018/0325618 A1 11/2018 Justin et al.
2018/0333073 A1 11/2018 Hill et al.
2018/0333207 A1 11/2018 Barrera
2018/0333208 A1 11/2018 Kotian et al.
2018/0344266 A1 12/2018 Altmann
2018/0344408 A1 12/2018 Rotilio et al.
2018/0357825 A1 12/2018 Hoffmann et al.
2018/0360310 A1 12/2018 Berlin
2018/0368930 A1 12/2018 Esterberg et al.
2019/0000564 A1 1/2019 Navab et al.
2019/0000570 A1 1/2019 Esterberg et al.
2019/0008592 A1 1/2019 Thienphrapa et al.
2019/0011709 A1 1/2019 Yadav et al.
2019/0015162 A1 1/2019 Abhari et al.
2019/0015167 A1 1/2019 Draelos et al.
2019/0029757 A1 1/2019 Roh et al.
2019/0035156 A1 1/2019 Wei et al.
2019/0038362 A1 2/2019 Nash et al.
2019/0046276 A1 2/2019 Inglese et al.
2019/0050665 A1 2/2019 Sakuragi
2019/0053851 A1 2/2019 Sieminonow et al.
2019/0053855 A1 2/2019 Siemionow et al.
2019/0053858 A1 2/2019 Kapoo et al.
2019/0054632 A1 2/2019 Grafenberg et al.
2019/0059773 A1 2/2019 Laughlin et al.
2019/0066260 A1 2/2019 Suehling et al.
2019/0066390 A1 2/2019 Vogel et al.
2019/0069962 A1 3/2019 Tabandeh et al.
2019/0076194 A1 3/2019 Jang
2019/0080515 A1 3/2019 Geri et al.
2019/0088162 A1 3/2019 Meglan
2019/0090955 A1 3/2019 Singh et al.
2019/0099221 A1 4/2019 Schmidt et al.
2019/0104919 A1 4/2019 Shelton, IV et al.
2019/0108654 A1 4/2019 Lasserre et al.
2019/0117190 A1 4/2019 Djajadonongrat
2019/0122443 A1 4/2019 Stocker
2019/0125361 A1 5/2019 Shelton, IV et al.
2019/0125454 A1 5/2019 Shelton, IV et al.
2019/0142520 A1 5/2019 Vandyken
2019/0159841 A1 5/2019 Abhari et al.
2019/0167148 A1 6/2019 Durfee et al.
2019/0175058 A1 6/2019 Godwin et al.
2019/0180441 A1 6/2019 Peng et al.
2019/0183576 A1 6/2019 Fahim et al.
2019/0183590 A1 6/2019 Hladio et al.
2019/0192230 A1 6/2019 Siemionow et al.
2019/0192232 A1 6/2019 Altmann et al.
2019/0200844 A1 7/2019 Shelton, IV et al.
2019/0200977 A1 7/2019 Shelton, IV et al.
2019/0201104 A1 7/2019 Shelton, IV et al.
2019/0201106 A1 7/2019 Siemionow et al.
2019/0201158 A1 7/2019 Shelton, IV et al.
2019/0206062 A1 7/2019 Matsuoka et al.
2019/0206134 A1 7/2019 Devam et al.
2019/0206565 A1 7/2019 Shelton, IV
2019/0209241 A1 7/2019 Begg
2019/0214126 A1 7/2019 Goetz
2019/0216572 A1 7/2019 Wang et al.
2019/0223746 A1 7/2019 Intrator
2019/0231220 A1 8/2019 Refai et al.
2019/0231443 A1 8/2019 McGinley et al.
2019/0239850 A1 8/2019 Dalvin et al.
2019/0254753 A1 8/2019 Johnson et al.
2019/0274762 A1 9/2019 Kim et al.
2019/0282099 A1 9/2019 Themelis
2019/0307516 A1 10/2019 Schotzko et al.
2020/0037943 A1* 2/2020 Chaja et al. .......... G06T 19/006

* cited by examiner

900
C-Arm Imaging Device 104
O-Arm Imaging Device 106
Image Database 950
Camera Tracking System Component 6/6'
Surgical Robot 4
Computer Platform 910
Network Interface 902
Display 912
Processor 914
Memory 916
Program code 918
920
920
920

POSE MEASUREMENT CHAINING FOR EXTENDED REALITY SURGICAL NAVIGATION IN VISIBLE AND NEAR INFRARED SPECTRUMS

FIELD

The present disclosure relates to medical devices and systems, and more particularly, computer assisted navigation in surgery.

BACKGROUND

Computer assisted navigation in surgery provides surgeons with enhanced visualization of surgical instruments with respect to radiographic images of the patient's anatomy. Navigated surgeries typically include components for tracking the position and orientation of surgical instruments via arrays of disks or spheres using a single near infrared (NIR) stereo camera setup. In this scenario, there are three parameters jointly competing for optimization: (1) accuracy, (2) robustness and (3) ergonomics.

Navigated surgery procedures using existing navigation systems are prone to events triggering intermittent pauses while personnel and/or objects obstruct the ability of a tracking component to track poses of the patient, the robot, and surgical instruments. There is a need to improve the tracking performance of navigation systems.

SUMMARY

Various embodiments disclosed herein are directed to improvements in computer assisted navigation during surgery. One or more extended reality (XR) headsets can be equipped with tracking cameras that provide tracking information to a camera tracking system for combining with tracking information from other tracking cameras which may be part of another XR headset, an auxiliary tracking bar, or other equipment. Through various pose chaining operations disclosed herein the camera tracking system may be able to track tools and other objects with greater robustness and through a wide range of motion.

In one embodiment, a surgical system includes a camera tracking system that is configured to receive tracking information related to tracked objects from a first tracking camera and a second tracking camera during a surgical procedure. The camera tracking system is configured to determine a first pose transform between a first object coordinate system and the first tracking camera coordinate system based on first object tracking information from the first tracking camera which indicates pose of the first object. The camera tracking system is configured to determine a second pose transform between the first object coordinate system and the second tracking camera coordinate system based on first object tracking information from the second tracking camera which indicates pose of the first object, and to determine a third pose transform between a second object coordinate system and the second tracking camera coordinate system based on second object tracking information from the second tracking camera which indicates pose of the second object. The camera tracking system is configured to determine a fourth pose transform between the second object coordinate system and the first tracking camera coordinate system based on combining the first, second, and third pose transforms.

Related methods by a camera tracking system and related computer program products are disclosed.

Other surgical systems, method, and computer program products according to embodiments will be or become apparent to one with skill in the art upon review of the following drawings and detailed description. It is intended that all such surgical systems, method, and computer program products be included within this description, be within the scope of the present disclosure, and be protected by the accompanying claims. Moreover, it is intended that all embodiments disclosed herein can be implemented separately or combined in any way and/or combination.

BRIEF DESCRIPTION OF THE DRAWINGS

The accompanying drawings, which are included to provide a further understanding of the disclosure and are incorporated in a constitute a part of this application, illustrate certain non-limiting embodiments of inventive concepts. In the drawings.

DETAILED DESCRIPTION

Inventive concepts will now be described more fully hereinafter with reference to the accompanying drawings, in which examples of embodiments of inventive concepts are shown. Inventive concepts may, however, be embodied in many different forms and should not be construed as limited to the embodiments set forth herein. Rather, these embodiments are provided so that this disclosure will be thorough and complete, and will fully convey the scope of various present inventive concepts to those skilled in the art. It should also be noted that these embodiments are not mutually exclusive. Components from one embodiment may be tacitly assumed to be present or used in another embodiment.

Various embodiments disclosed herein are directed to improvements in computer assisted navigation during surgery. An extended reality (XR) headset is operatively connected to the surgical system and configured to provide an interactive environment through which a surgeon, assistant, and/or other personnel can view and select among patient images, view and select among computer generated surgery navigation information, and/or control surgical equipment in the operating room. As will be explained below, the XR headset may be configured to augment a real-world scene with computer generated XR images. The XR headset may be configured to provide an augmented reality (AR) viewing environment by displaying the computer generated XR images on a see-through display screen that allows light from the real-world scene to pass therethrough for combined viewing by the user. Alternatively, the XR headset may be configured to provide a virtual reality (VR) viewing environment by preventing or substantially preventing light from the real-world scene from being directly viewed by the user while the user is viewing the computer generated AR images on a display screen. An XR headset can be configured to provide both AR and VR viewing environments. In one embodiment, both AR and VR viewing environments are provided by lateral bands of substantially differing opacity arranged between the see-through display screen and the real-world scene, so that a VR viewing environment is provided for XR images aligned with a high opacity band and an AR viewing environment is provided for XR images aligned with the low opacity band. In another embodiment, both AR and VR viewing environments are provided by computer adjustable control of an opacity filter that variably constrains how much light from the real-world scene passes through a see-through display screen for combining with the XR images viewed by the user. Thus, the XR headset can also be referred to as an AR headset or a VR headset.

Figure 1:
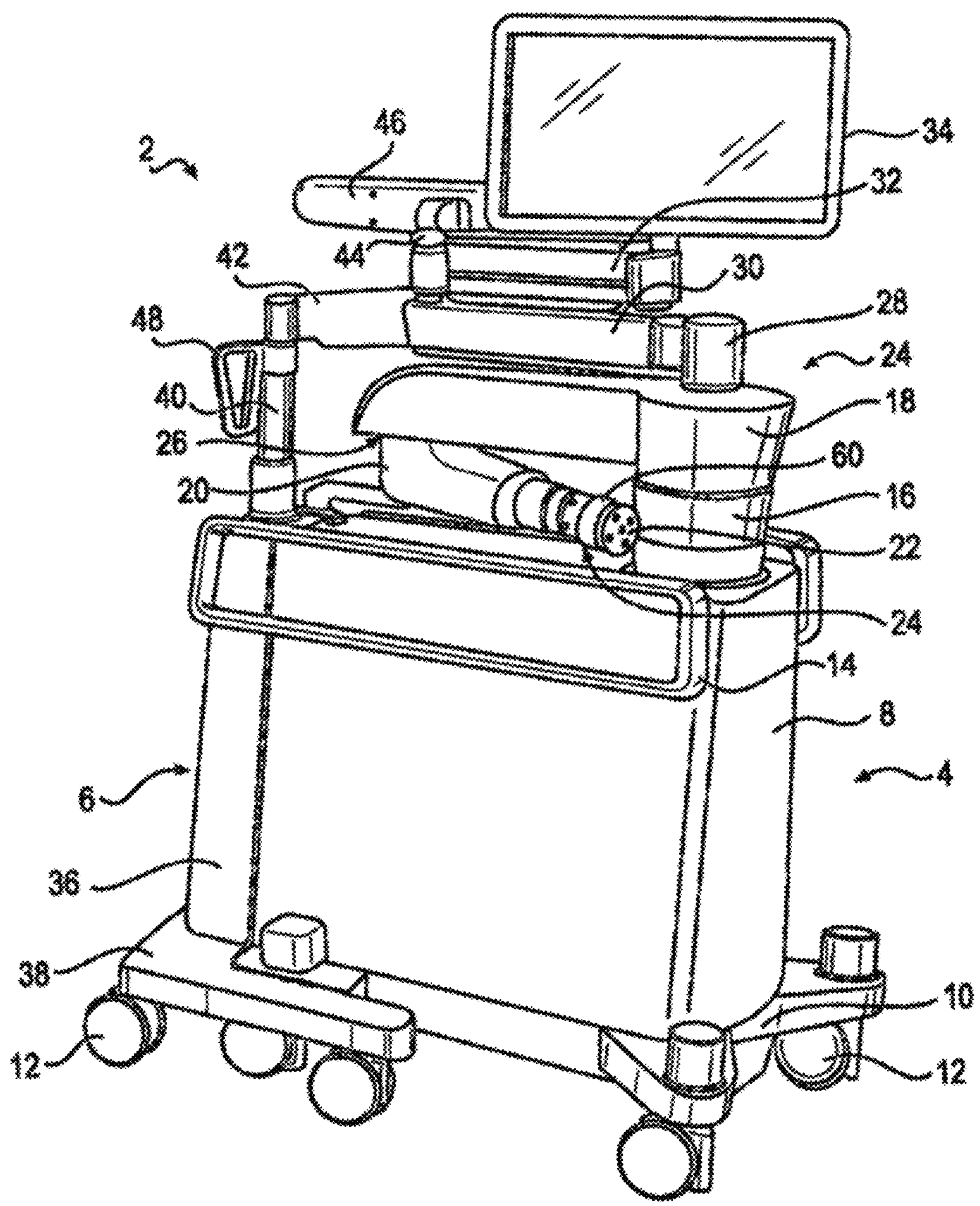
FIG. 1 illustrates an embodiment of a surgical system according to some embodiments of the present disclosure.

FIG. 1 illustrates an embodiment of a surgical system 2 according to some embodiments of the present disclosure. Prior to performance of an orthopedic or other surgical procedure, a three-dimensional ("3D") image scan may be taken of a planned surgical area of a patient using, e.g., the C-Arm imaging device 104 of FIG. 10 or O-Arm imaging device 106 of FIG. 11, or from another medical imaging device such as a computed tomography (CT) image or MRI. This scan can be taken pre-operatively (e.g. few weeks before procedure, most common) or intra-operatively. However, any known 3D or 2D image scan may be used in accordance with various embodiments of the surgical system 2. The image scan is sent to a computer platform in communication with the surgical system 2, such as the computer platform 910 of the surgical system 900 (FIG. 9) which may include the camera tracking system component 6, the surgical robot 4 (e.g., robot 2 in FIG. 1), imaging devices (e.g., C-Arm 104, O-Arm 106, etc.), and an image database 950 for storing image scans of patients. A surgeon reviewing the image scan(s) on a display device of the computer platform 910 (FIG. 9) generates a surgical plan defining a target pose for a surgical tool to be used during a surgical procedure on an anatomical structure of the patient. Example surgical tools, also referred to as tools, can include, without limitation, drills, screw drivers, retractors, and implants such as a screws, spacers, interbody fusion devices, plates, rods, etc. In some embodiments, the surgical plan defining the target plane is planned on the 3D image scan displayed on a display device.

As used herein, the term "pose" refers to the position and/or the rotational angle of one object (e.g., dynamic reference array, end effector, surgical tool, anatomical structure, etc.) relative to another object and/or to a defined coordinate system. A pose may therefore be defined based on only the multidimensional position of one object relative to another object and/or to a defined coordinate system, only on the multidimensional rotational angles of the object relative to another object and/or to a defined coordinate system, or on a combination of the multidimensional position and the multidimensional rotational angles. The term "pose" therefore is used to refer to position, rotational angle, or combination thereof.

The surgical system 2 of FIG. 1 can assist surgeons during medical procedures by, for example, holding tools, aligning tools, using tools, guiding tools, and/or positioning tools for use. In some embodiments, surgical system 2 includes a surgical robot 4 and a camera tracking system component 6. The ability to mechanically couple surgical robot 4 and camera tracking system component 6 can allow for surgical system 2 to maneuver and move as a single unit, and allow surgical system 2 to have a small footprint in an area, allow easier movement through narrow passages and around turns, and allow storage within a smaller area.

A surgical procedure may begin with the surgical system 2 moving from medical storage to a medical procedure room. The surgical system 2 may be maneuvered through doorways, halls, and elevators to reach a medical procedure room. Within the room, the surgical system 2 may be physically separated into two separate and distinct systems, the surgical robot 4 and the camera tracking system component 6. Surgical robot 4 may be positioned adjacent the patient at any suitable location to properly assist medical personnel. Camera tracking system component 6 may be positioned at the base of the patient, at the patient shoulders, or any other location suitable to track the present pose and movement of the pose of tracks portions of the surgical robot 4 and the patient. Surgical robot 4 and camera tracking system component 6 may be powered by an onboard power source and/or plugged into an external wall outlet.

Surgical robot 4 may be used to assist a surgeon by holding and/or using tools during a medical procedure. To properly utilize and hold tools, surgical robot 4 may rely on a plurality of motors, computers, and/or actuators to function properly. Illustrated in FIG. 1, robot body 8 may act as the structure in which the plurality of motors, computers, and/or actuators may be secured within surgical robot 4. Robot body 8 may also provide support for robot telescoping support arm 16. The size of robot body 8 may provide a solid platform supporting attached components, and may house, conceal, and protect the plurality of motors, computers, and/or actuators that may operate attached components.

Robot base 10 may act as a lower support for surgical robot 4. In some embodiments, robot base 10 may support robot body 8 and may attach robot body 8 to a plurality of powered wheels 12. This attachment to wheels may allow robot body 8 to move in space efficiently. Robot base 10 may run the length and width of robot body 8. Robot base 10 may be about two inches to about 10 inches tall. Robot base 10 may cover, protect, and support powered wheels 12.

In some embodiments, as illustrated in FIG. 1, at least one powered wheel 12 may be attached to robot base 10. Powered wheels 12 may attach to robot base 10 at any location. Each individual powered wheel 12 may rotate about a vertical axis in any direction. A motor may be disposed above, within, or adjacent to powered wheel 12. This motor may allow for surgical system 2 to maneuver into any location and stabilize and/or level surgical system 2. A rod, located within or adjacent to powered wheel 12, may be pressed into a surface by the motor. The rod, not pictured, may be made of any suitable metal to lift surgical system 2. The rod may lift powered wheel 10, which may lift surgical system 2, to any height required to level or otherwise fix the orientation of the surgical system 2 in relation to a patient. The weight of surgical system 2, supported through small contact areas by the rod on each wheel, prevents surgical system 2 from moving during a medical procedure. This rigid positioning may prevent objects and/or people from moving surgical system 2 by accident.

Moving surgical system 2 may be facilitated using robot railing 14. Robot railing 14 provides a person with the ability to move surgical system 2 without grasping robot body 8. As illustrated in FIG. 1, robot railing 14 may run the length of robot body 8, shorter than robot body 8, and/or may run longer the length of robot body 8. Robot railing 14 may further provide protection to robot body 8, preventing objects and or personnel from touching, hitting, or bumping into robot body 8.

Robot body 8 may provide support for a Selective Compliance Articulated Robot Arm, hereafter referred to as a "SCARA." A SCARA 24 may be beneficial to use within the surgical system 2 due to the repeatability and compactness of the robotic arm. The compactness of a SCARA may provide additional space within a medical procedure, which may allow medical professionals to perform medical procedures free of excess clutter and confining areas. SCARA 24 may comprise robot telescoping support 16, robot support arm 18, and/or robot arm 20. Robot telescoping support 16 may be disposed along robot body 8. As illustrated in FIG. 1, robot telescoping support 16 may provide support for the SCARA 24 and display 34. In some embodiments, robot telescoping support 16 may extend and contract in a vertical direction. The body of robot telescoping support 16 may be any width and/or height configured to support the stress and weight placed upon it.

In some embodiments, medical personnel may move SCARA 24 through a command submitted by the medical personnel. The command may originate from input received on display 34, a tablet, and/or an XR headset (e.g., headset 920 in FIG. 9) as will be explained in further detail below. The XR headset may eliminate the need for medical personnel to refer to any other display such as the display 34 or a tablet, which enables the SCARA 24 to be configured without the display 34 and/or the tablet. The command may be generated by the depression of a switch and/or the depression of a plurality of switches, and/or may be generated based on a hand gesture command and/or voice command that is sensed by the XR headset as will be explained in further detail below.

Figure 5:
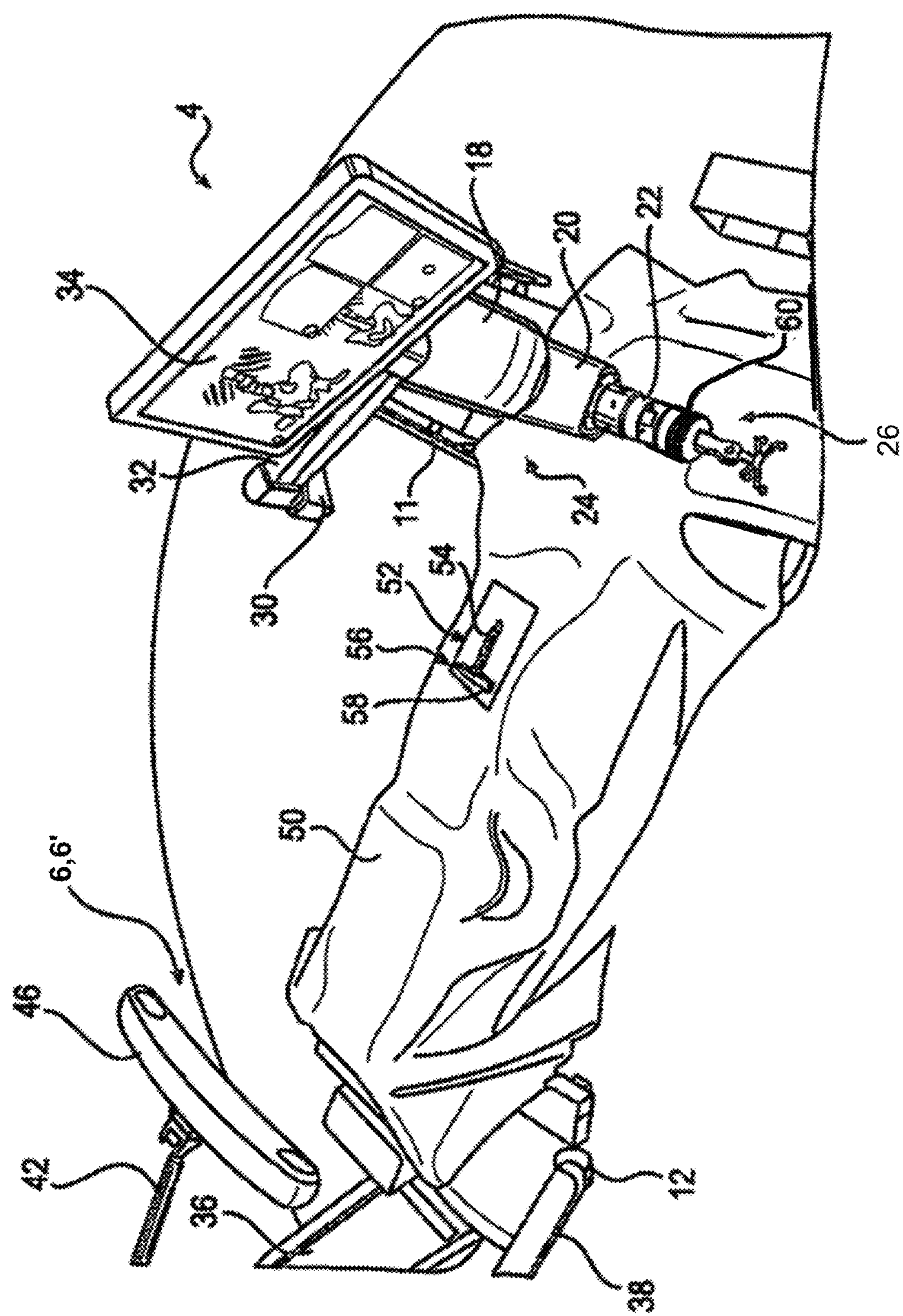
FIG. 5 illustrates a medical operation in which a surgical robot and a camera system are disposed around a patient.

As shown in FIG. 5, an activation assembly 60 may include a switch and/or a plurality of switches. The activation assembly 60 may be operable to transmit a move command to the SCARA 24 allowing an operator to manually manipulate the SCARA 24. When the switch, or plurality of switches, is depressed the medical personnel may have the ability to move SCARA 24 through applied hand movements. Alternatively or additionally, an operator may control movement of the SCARA 24 through hand gesture commands and/or voice commands that are sensed by the XR headset as will be explained in further detail below. Additionally, when the SCARA 24 is not receiving a command to move, the SCARA 24 may lock in place to prevent accidental movement by personnel and/or other objects. By locking in place, the SCARA 24 provides a solid platform through which the end effector 26 can guide a surgical tool during a medical procedure.

Robot support arm 18 can be connected to robot telescoping support 16 by various mechanisms. In some embodiments, best seen in FIGS. 1 and 2, robot support arm 18 rotates in any direction in regard to robot telescoping support 16. Robot support arm 18 may rotate three hundred and sixty degrees around robot telescoping support 16. Robot arm 20 may connect to robot support arm 18 at any suitable location and by various mechanisms that enable rotation in any direction relative to robot support arm 18. In one embodiment, the robot arm 20 can rotate three hundred and sixty degrees relative to the robot support arm 18. This free rotation allows an operator to position robot arm 20 according to a surgical plan.

Figure 4:
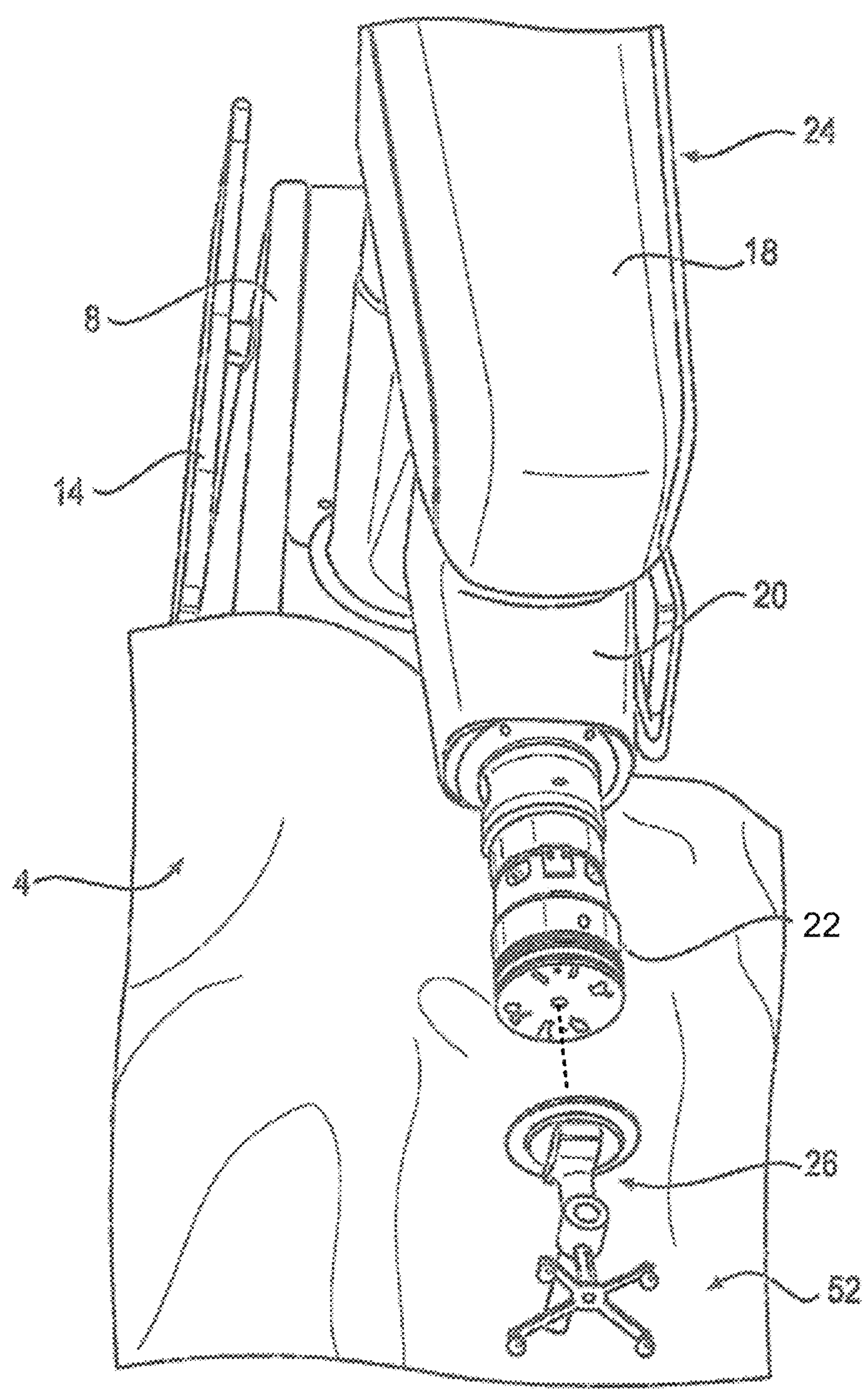
FIG. 4 illustrates an embodiment of an end effector that is connectable to a robot arm and configured according to some embodiments of the present disclosure.

The end effector 26 shown in FIGS. 4 and 5 may attach to robot arm 20 in any suitable location. The end effector 26 can be configured to attach to an end effector coupler 22 of the robot arm 20 positioned by the surgical robot 4. The example end effector 26 includes a tubular guide that guides movement of an inserted surgical tool relative to an anatomical structure on which a surgical procedure is to be performed.

In some embodiments, a dynamic reference array 52 is attached to the end effector 26. Dynamic reference arrays, also referred to as "DRAB" herein, are rigid bodies which may be disposed on an anatomical structure (e.g., bone) of a patient, one or more XR headsets being worn by personnel in the operating room, the end effector, the surgical robot, a surgical tool in a navigated surgical procedure. The computer platform 910 in combination with the camera tracking system component 6 or other 3D localization system are configured to track in real-time the pose (e.g., positions and rotational orientations) of the DRA. The DRA can include fiducials, such as the illustrated arrangement of balls. This tracking of 3D coordinates of the DRA can allow the surgical system 2 to determine the pose of the DRA in any multidimensional space in relation to the target anatomical structure of the patient 50 in FIG. 5.

Figure 2:
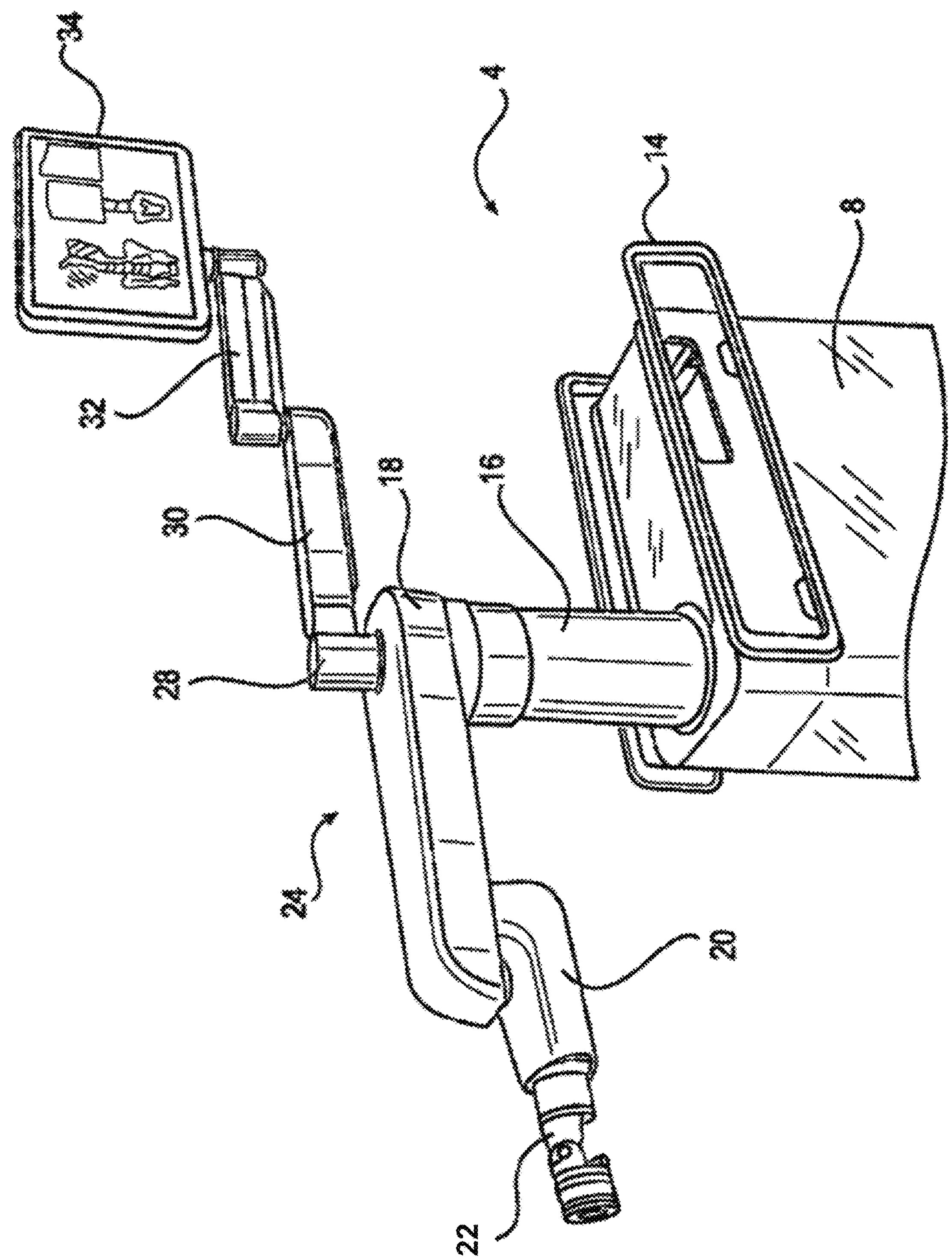
FIG. 2 illustrates a surgical robot component of the surgical system of FIG. 1 according to some embodiments of the present disclosure.

As illustrated in FIG. 1, a light indicator 28 may be positioned on top of the SCARA 24. Light indicator 28 may illuminate as any type of light to indicate "conditions" in which surgical system 2 is currently operating. In some embodiments, the light may be produced by LED bulbs, which may form a ring around light indicator 28. Light indicator 28 may comprise a fully permeable material that can let light shine through the entirety of light indicator 28. Light indicator 28 may be attached to lower display support 30. Lower display support 30, as illustrated in FIG. 2 may allow an operator to maneuver display 34 to any suitable location. Lower display support 30 may attach to light indicator 28 by any suitable mechanism. In some embodiments, lower display support 30 may rotate about light indicator 28 or be rigidly attached thereto. Upper display support 32 may attach to lower display support 30 by any suitable mechanism.

In some embodiments, a tablet may be used in conjunction with display 34 and/or without display 34. The tablet may be disposed on upper display support 32, in place of display 34, and may be removable from upper display support 32 during a medical operation. In addition the tablet may communicate with display 34. The tablet may be able to connect to surgical robot 4 by any suitable wireless and/or wired connection. In some embodiments, the tablet may be able to program and/or control surgical system 2 during a medical operation. When controlling surgical system 2 with the tablet, all input and output commands may be duplicated on display 34. The use of a tablet may allow an operator to manipulate surgical robot 4 without having to move around patient 50 and/or to surgical robot 4.

As will be explained below, in some embodiments a surgeon and/or other personnel can wear XR headsets that may be used in conjunction with display 34 and/or a tablet or the XR head(s) may eliminate the need for use of the display 34 and/or tablet.

Figure 3A:
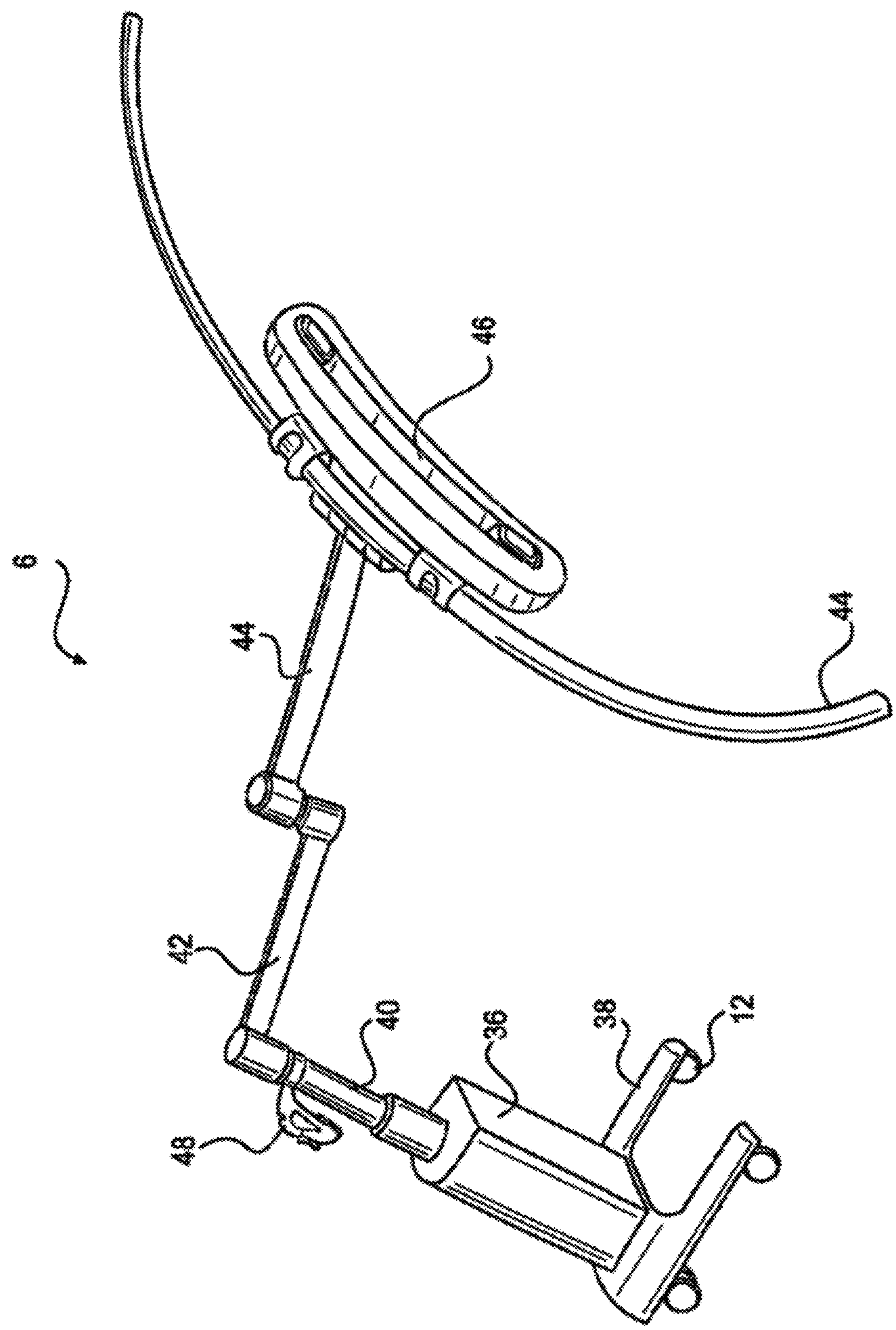
FIG. 3A illustrates a camera tracking system component of the surgical system of FIG. 1 according to some embodiments of the present disclosure.

As illustrated in FIGS. 3A and 5, camera tracking system component 6 works in conjunction with surgical robot 4 through wired or wireless communication networks. Referring to FIGS. 1, 3 and 5, camera tracking system component 6 can include some similar components to the surgical robot 4. For example, camera body 36 may provide the functionality found in robot body 8. Robot body 8 may provide an auxiliary tracking bar upon which cameras 46 are mounted. The structure within robot body 8 may also provide support for the electronics, communication devices, and power supplies used to operate camera tracking system component 6. Camera body 36 may be made of the same material as robot body 8. Camera tracking system component 6 may communicate directly to an XR headset, tablet and/or display 34 by a wireless and/or wired network to enable the XR headset, tablet and/or display 34 to control the functions of camera tracking system component 6.

Camera body 36 is supported by camera base 38. Camera base 38 may function as robot base 10. In the embodiment of FIG. 1, camera base 38 may be wider than robot base 10. The width of camera base 38 may allow for camera tracking system component 6 to connect with surgical robot 4. As illustrated in FIG. 1, the width of camera base 38 may be large enough to fit outside robot base 10. When camera tracking system component 6 and surgical robot 4 are connected, the additional width of camera base 38 may allow surgical system 2 additional maneuverability and support for surgical system 2.

As with robot base 10, a plurality of powered wheels 12 may attach to camera base 38. Powered wheel 12 may allow camera tracking system component 6 to stabilize and level or set fixed orientation in regards to patient 50, similar to the operation of robot base 10 and powered wheels 12. This stabilization may prevent camera tracking system component 6 from moving during a medical procedure and may keep cameras 46 on the auxiliary tracking bar from losing track of a DRA connected to an XR headset and/or the surgical robot 4, and/or losing track of one or more DRAs 52 connected to an anatomical structure 54 and/or tool 58 within a designated area 56 as shown in FIGS. 3A and 5. This stability and maintenance of tracking enhances the ability of surgical robot 4 to operate effectively with camera tracking system component 6. Additionally, the wide camera base 38 may provide additional support to camera tracking system component 6. Specifically, a wide camera base 38 may prevent camera tracking system component 6 from tipping over when cameras 46 is disposed over a patient, as illustrated in FIGS. 3A and 5.

Camera telescoping support 40 may support cameras 46 on the auxiliary tracking bar. In some embodiments, telescoping support 40 moves cameras 46 higher or lower in the vertical direction. Camera handle 48 may be attached to camera telescoping support 40 at any suitable location and configured to allow an operator to move camera tracking system component 6 into a planned position before a medical operation. In some embodiments, camera handle 48 is used to lower and raise camera telescoping support 40. Camera handle 48 may perform the raising and lowering of camera telescoping support 40 through the depression of a button, switch, lever, and/or any combination thereof.

Lower camera support arm 42 may attach to camera telescoping support 40 at any suitable location, in embodiments, as illustrated in FIG. 1, lower camera support arm 42 may rotate three hundred and sixty degrees around telescoping support 40. This free rotation may allow an operator to position cameras 46 in any suitable location. Lower camera support arm 42 may connect to telescoping support 40 by any suitable mechanism. Lower camera support arm 42 may be used to provide support for cameras 46. Cameras 46 may be attached to lower camera support arm 42 by any suitable mechanism. Cameras 46 may pivot in any direction at the attachment area between cameras 46 and lower camera support arm 42. In embodiments a curved rail 44 may be disposed on lower camera support arm 42.

Curved rail 44 may be disposed at any suitable location on lower camera support arm 42. As illustrated in FIG. 3A, curved rail 44 may attach to lower camera support arm 42 by any suitable mechanism. Curved rail 44 may be of any suitable shape, a suitable shape may be a crescent, circular, oval, elliptical, and/or any combination thereof. Cameras 46 may be moveably disposed along curved rail 44. Cameras 46 may attach to curved rail 44 by, for example, rollers, brackets, braces, motors, and/or any combination thereof. Motors and rollers, not illustrated, may be used to move cameras 46 along curved rail 44. As illustrated in FIG. 3A, during a medical procedure, if an object prevents cameras 46 from viewing one or more DRAs being tracked, the motors may responsively move cameras 46 along curved rail 44. This motorized movement may allow cameras 46 to move to a new position that is no longer obstructed by the object without moving camera tracking system component 6. While cameras 46 is obstructed from viewing one or more tracked DRAs, camera tracking system component 6 may send a stop signal to a surgical robot 4, XR headset, display 34, and/or a tablet. The stop signal may prevent SCARA 24 from moving until cameras 46 has reacquired tracked DRAs 52 and/or can warn an operator wearing the XR headset and/or viewing the display 34 and/or the tablet. This SCARA 24 can be configured to respond to receipt of a stop signal by stopping further movement of the base and/or end effector coupler 22 until the camera tracking system can resume tracking of DRAs.

Figure 3C:
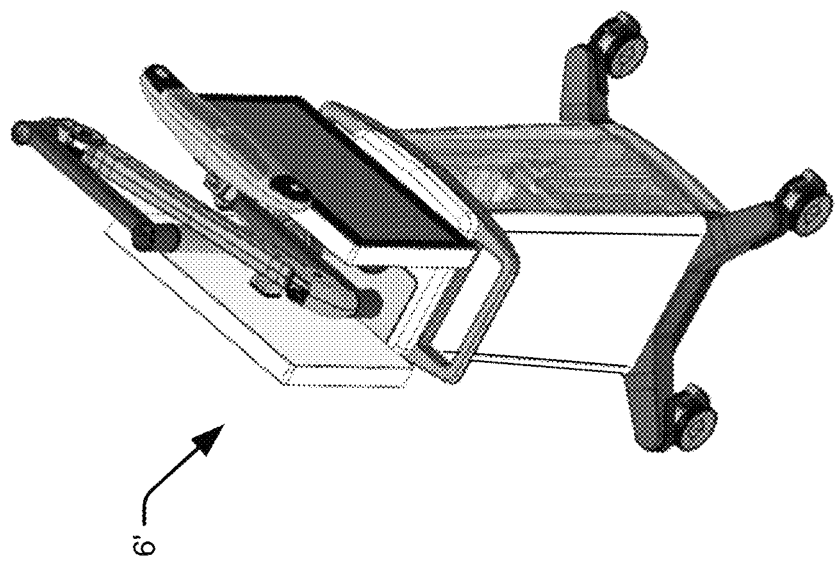
FIGS. 3B and 3C illustrate a front view and isometric view of another camera tracking system component which may be used with the surgical system of FIG. 1 according to some embodiments of the present disclosure.
Figure 3B:
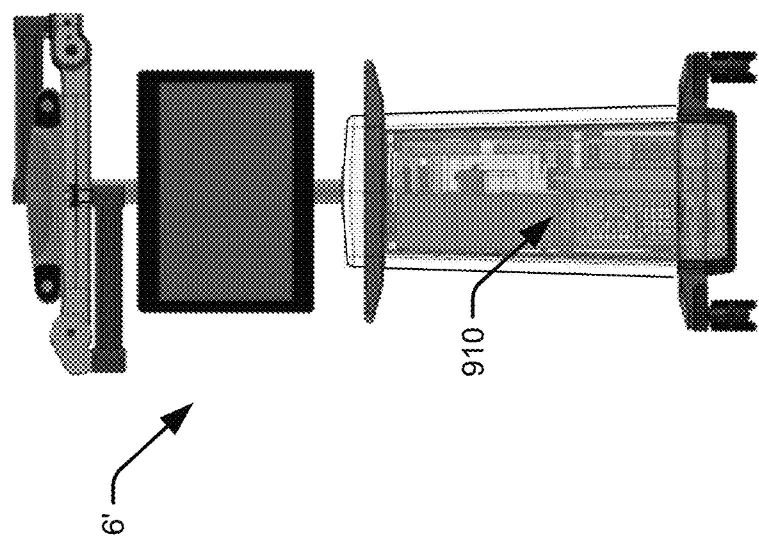

FIGS. 3B and 3C illustrate a front view and isometric view of another camera tracking system component 6' which may be used with the surgical system of FIG. 1 or may be used independent of a surgical robot. For example, the camera tracking system component 6' may be used for providing navigated surgery without use of robotic guidance. One of the differences between the camera tracking system component 6' of FIGS. 3B and 3C and the camera tracking system component 6 of FIG. 3A, is that the camera tracking system component 6' of FIGS. 3B and 3C includes a housing that transports the computer platform 910. The computer platform 910 can be configured to perform camera tracking operations to track DRAs, perform navigated surgery operations that provide surgical navigation information to a display device, e.g., XR headset and/or other display device, and perform other computational operations disclosed herein. The computer platform 910 can therefore include a navigation computer, such as one or more of the navigation computers of FIG. 14.

Figure 6:
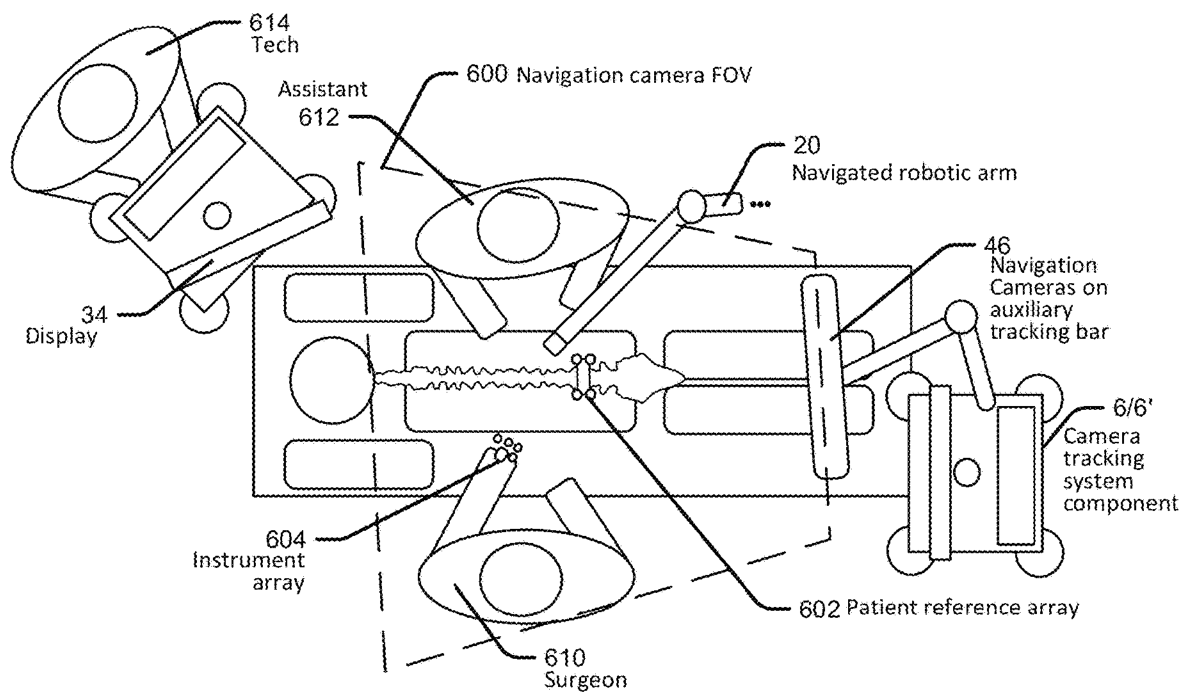
FIG. 6 illustrates a block diagram view of the components of the surgical system of FIG. 5 being used for a medical operation.

FIG. 6 illustrates a block diagram view of the components of the surgical system of FIG. 5 used for the medical operation. Referring to FIG. 6, the navigation cameras 46 on the auxiliary tracking bar has a navigation field-of-view 600 in which the pose (e.g., position and orientation) of the reference array 602 attached to the patient, the reference array 604 attached to the surgical instrument, and the robot arm 20 are tracked. The navigation cameras 46 may be part of the camera tracking system component 6' of FIGS. 3B and 3C, which includes the computer platform 910 configured to perform the operations described below. The reference arrays enable tracking by reflecting light in known patterns, which are decoded to determine their respective poses by the tracking subsystem of the surgical robot 4. If the line-of-sight between the patient reference array 602 and the navigation cameras 46 in the auxiliary tracking bar is blocked (for example, by a medical personnel, instrument, etc.), further navigation of the surgical instrument may not be able to be performed and a responsive notification may temporarily halt further movement of the robot arm 20 and surgical robot 4, display a warning on the display 34, and/or provide an audible warning to medical personnel. The display 34 is accessible to the surgeon 610 and assistant 612 but viewing requires a head to be turned away from the patient and for eye focus to be changed to a different distance and location. The navigation software may be controlled by a tech personnel 614 based on vocal instructions from the surgeon.

Figure 7:
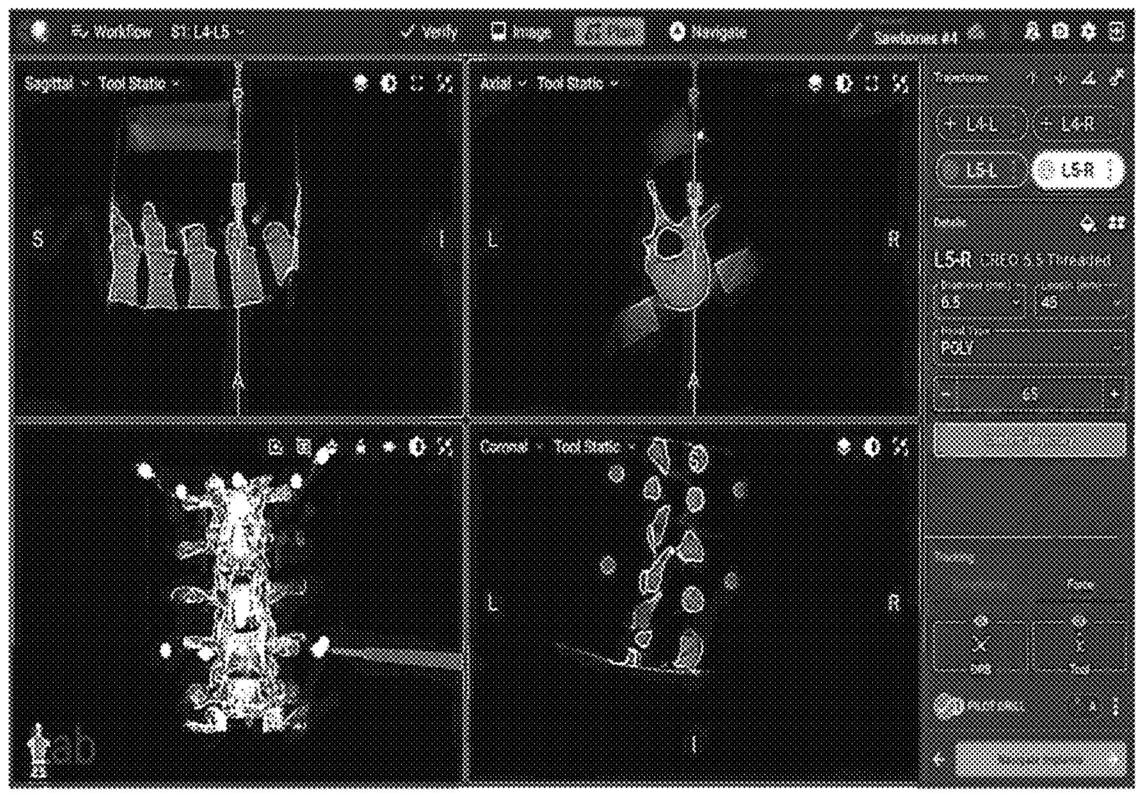
FIG. 7 illustrates various display screens that may be displayed on the display of FIGS. 5 and 6 when using a navigation function of the surgical system.

FIG. 7 illustrates various display screens that may be displayed on the display 34 of FIGS. 5 and 6 by the surgical robot 4 when using a navigation function of the surgical system 2. The display screens can include, without limitation, patient radiographs with overlaid graphical representations of models of instruments that are positioned in the display screens relative to the anatomical structure based on a developed surgical plan and/or based on poses of tracked reference arrays, various user selectable menus for controlling different stages of the surgical procedure and dimension parameters of a virtually projected implant (e.g. length, width, and/or diameter).

For navigated surgery, various processing components (e.g., computer platform 910) and associated software described below are provided that enable pre-operatively planning of a surgical procedure, e.g., implant placement, and electronic transfer of the plan to computer platform 910 to provide navigation information to one or more users during the planned surgical procedure.

For robotic navigation, various processing components (e.g., computer platform 910) and associated software described below are provided that enable pre-operatively planning of a surgical procedure, e.g., implant placement, and electronic transfer of the plan to the surgical robot 4. The surgical robot 4 uses the plan to guide the robot arm 20 and connected end effector 26 to provide a target pose for a surgical tool relative to a patient anatomical structure for a step of the planned surgical procedure.

Various embodiments below are directed to using one or more XR headsets that can be worn by the surgeon 610, the assistant 612, and/or other medical personnel to provide an improved user interface for receiving information from and/or providing control commands to the surgical robot, the camera tracking system component 6/6', and/or other medical equipment in the operating room.

Figure 8:
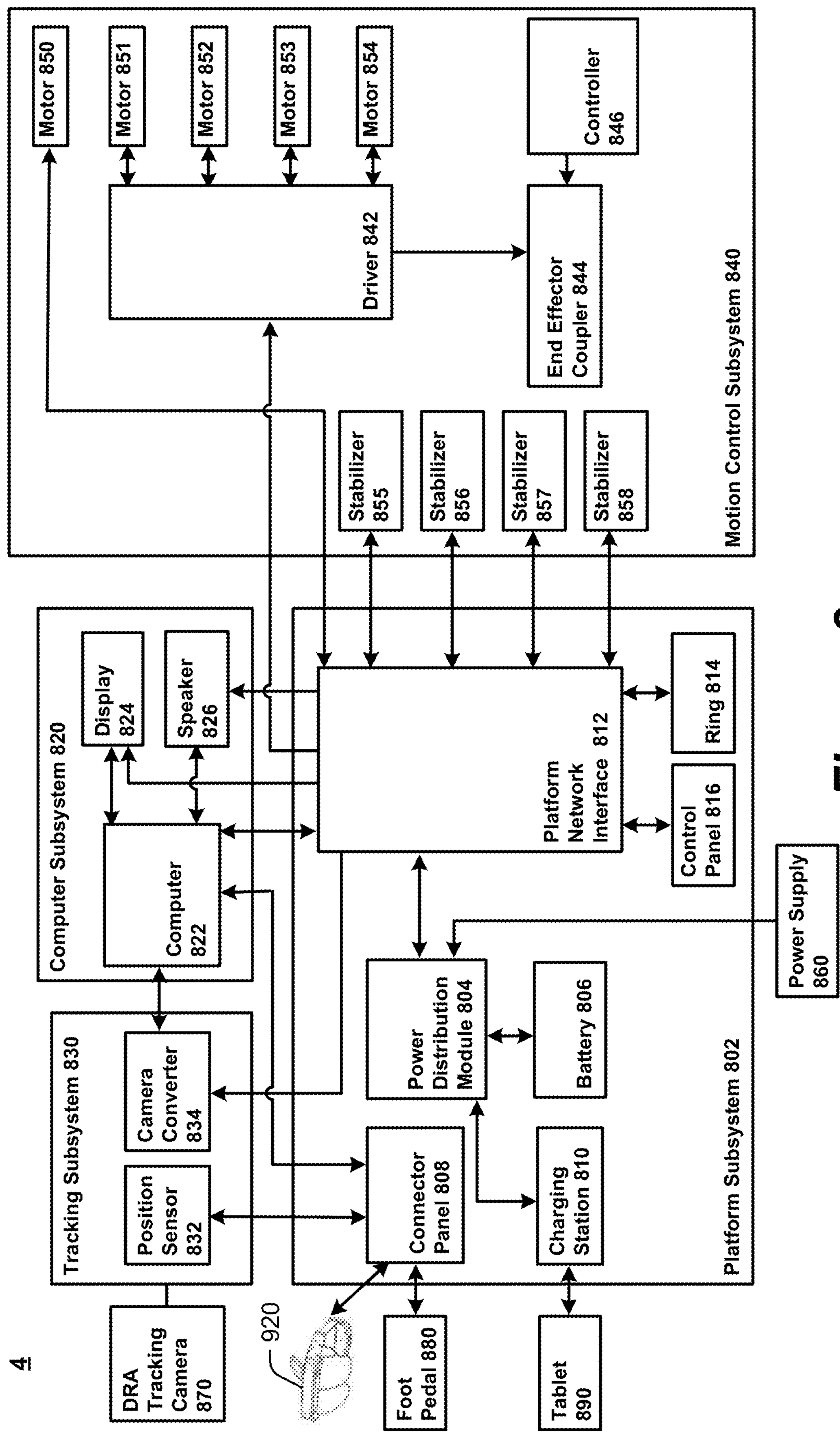
FIG. 8 illustrates a block diagram of some electrical components of a surgical robot according to some embodiments of the present disclosure.

FIG. 8 illustrates a block diagram of some electrical components of the surgical robot 4 according to some embodiments of the present disclosure. Referring to FIG. 8, a load cell (not shown) may be configured to track force applied to end effector coupler 22. In some embodiments the load cell may communicate with a plurality of motors 850, 851, 852, 853, and/or 854. As load cell senses force, information as to the amount of force applied may be distributed from a switch array and/or a plurality of switch arrays to a controller 846. Controller 846 may take the force information from load cell and process it with a switch algorithm. The switch algorithm is used by the controller 846 to control a motor driver 842. The motor driver 842 controls operation of one or more of the motors 850, 851, 852, 853, and 854. Motor driver 842 may direct a specific motor to produce, for example, an equal amount of force measured by load cell through the motor. In some embodiments, the force produced may come from a plurality of motors, e.g., 850-854, as directed by controller 846. Additionally, motor driver 842 may receive input from controller 846. Controller 846 may receive information from load cell as to the direction of force sensed by load cell. Controller 846 may process this information using a motion controller algorithm. The algorithm may be used to provide information to specific motor drivers 842. To replicate the direction of force, controller 846 may activate and/or deactivate certain motor drivers 842. Controller 846 may control one or more motors, e.g. one or more of 850-854, to induce motion of end effector 26 in the direction of force sensed by load cell. This force-controlled motion may allow an operator to move SCARA 24 and end effector 26 effortlessly and/or with very little resistance. Movement of end effector 26 can be performed to position end effector 26 in any suitable pose (i.e., location and angular orientation relative to defined three-dimensional (3D) orthogonal reference axes) for use by medical personnel.

Activation assembly 60, best illustrated in FIG. 5, may form of a bracelet that wraps around end effector coupler 22. The activation assembly 60 may be located on any part of SCARA 24, any part of end effector coupler 22, may be worn by medical personnel (and communicate wirelessly), and/or any combination thereof. Activation assembly 60 may comprise of a primary button and a secondary button.

Depressing primary button may allow an operator to move SCARA 24 and end effector coupler 22. According to one embodiment, once set in place, SCARA 24 and end effector coupler 22 may not move until an operator programs surgical robot 4 to move SCARA 24 and end effector coupler 22, or is moved using primary button. In some examples, it may require the depression of at least two non-adjacent primary activation switches before SCARA 24 and end effector coupler 22 will respond to operator commands. Depression of at least two primary activation switches may prevent the accidental movement of SCARA 24 and end effector coupler 22 during a medical procedure.

Activated by primary button, load cell may measure the force magnitude and/or direction exerted upon end effector coupler 22 by an operator, i.e. medical personnel. This information may be transferred to one or more motors, e.g. one or more of 850-854, within SCARA 24 that may be used to move SCARA 24 and end effector coupler 22. Information as to the magnitude and direction of force measured by load cell may cause the one or more motors, e.g. one or more of 850-854, to move SCARA 24 and end effector coupler 22 in the same direction as sensed by the load cell. This force-controlled movement may allow the operator to move SCARA 24 and end effector coupler 22 easily and without large amounts of exertion due to the motors moving SCARA 24 and end effector coupler 22 at the same time the operator is moving SCARA 24 and end effector coupler 22.

In some examples, a secondary button may be used by an operator as a "selection" device. During a medical operation, surgical robot 4 may notify medical personnel to certain conditions by the XR headset(s) 920, display 34 and/or light indicator 28. The XR headset(s) 920 are each configured to display images on a see-through display screen to form an extended reality image that is overlaid on real-world objects viewable through the see-through display screen. Medical personnel may be prompted by surgical robot 4 to select a function, mode, and/or asses the condition of surgical system 2. Depressing secondary button a single time may activate certain functions, modes, and/or acknowledge information communicated to medical personnel through the XR headset(s) 920, display 34 and/or light indicator 28. Additionally, depressing the secondary button multiple times in rapid succession may activate additional functions, modes, and/or select information communicated to medical personnel through the XR headset(s) 920, display 34 and/or light indicator 28.

With further reference to FIG. 8, electrical components of the surgical robot 4 include platform subsystem 802, computer subsystem 820, motion control subsystem 840, and tracking subsystem 830. Platform subsystem 802 includes battery 806, power distribution module 804, connector panel 808, and charging station 810. Computer subsystem 820 includes computer 822, display 824, and speaker 826. Motion control subsystem 840 includes driver circuit 842, motors 850, 851, 852, 853, 854, stabilizers 855, 856, 857, 858, end effector connector 844, and controller 846. Tracking subsystem 830 includes position sensor 832 and camera converter 834. Surgical robot 4 may also include a removable foot pedal 880 and removable tablet computer 890.

Input power is supplied to surgical robot 4 via a power source which may be provided to power distribution module 804. Power distribution module 804 receives input power and is configured to generate different power supply voltages that are provided to other modules, components, and subsystems of surgical robot 4. Power distribution module 804 may be configured to provide different voltage supplies to connector panel 808, which may be provided to other components such as computer 822, display 824, speaker 826, driver 842 to, for example, power motors 850-854 and end effector coupler 844, and provided to camera converter 834 and other components for surgical robot 4. Power distribution module 804 may also be connected to battery 806, which serves as temporary power source in the event that power distribution module 804 does not receive power from an input power. At other times, power distribution module 804 may serve to charge battery 806.

Connector panel 808 may serve to connect different devices and components to surgical robot 4 and/or associated components and modules. Connector panel 808 may contain one or more ports that receive lines or connections from different components. For example, connector panel 808 may have a ground terminal port that may ground surgical robot 4 to other equipment, a port to connect foot pedal 880, a port to connect to tracking subsystem 830, which may include position sensor 832, camera converter 834, and DRA tracking cameras 870. Connector panel 808 may also include other ports to allow USB, Ethernet, HDMI communications to other components, such as computer 822. In accordance with some embodiments, the connector panel 808 can include a wired and/or wireless interface for operatively connecting one or more XR headsets 920 to the tracking subsystem 830 and/or the computer subsystem 820.

Control panel 816 may provide various buttons or indicators that control operation of surgical robot 4 and/or provide information from surgical robot 4 for observation by an operator. For example, control panel 816 may include buttons to power on or off surgical robot 4, lift or lower vertical column 16, and lift or lower stabilizers 855-858 that may be designed to engage casters 12 to lock surgical robot 4 from physically moving. Other buttons may stop surgical robot 4 in the event of an emergency, which may remove all motor power and apply mechanical brakes to stop all motion from occurring. Control panel 816 may also have indicators notifying the operator of certain system conditions such as a line power indicator or status of charge for battery 806. In accordance with some embodiments, one or more XR headsets 920 may communicate, e.g. via the connector panel 808, to control operation of the surgical robot 4 and/or to received and display information generated by surgical robot 4 for observation by persons wearing the XR headsets 920.

Computer 822 of computer subsystem 820 includes an operating system and software to operate assigned functions of surgical robot 4. Computer 822 may receive and process information from other components (for example, tracking subsystem 830, platform subsystem 802, and/or motion control subsystem 840) in order to display information to the operator. Further, computer subsystem 820 may provide output through the speaker 826 for the operator. The speaker may be part of the surgical robot, part of an XR headset 920, or within another component of the surgical system 2. The display 824 may correspond to the display 34 shown in FIGS. 1 and 2.

Tracking subsystem 830 may include position sensor 832 and camera converter 834. Tracking subsystem 830 may correspond to the camera tracking system component 6 of FIG. 3. The DRA tracking cameras 870 operate with the position sensor 832 to determine the pose of DRAs 52. This tracking may be conducted in a manner consistent with the present disclosure including the use of infrared or visible light technology that tracks the location of active or passive elements of DRAs 52, such as LEDs or reflective markers, respectively.

Functional operations of the tracking subsystem 830 and the computer subsystem 820 can be included in the computer platform 910, which can be transported by the camera tracking system component 6' of FIGS. 3A and 3B. The tracking subsystem 830 can be configured to determine the poses, e.g., location and angular orientation of the tracked DRAs. The computer platform 910 can also include a navigation controller that is configured to use the determined poses to provide navigation information to users that guides their movement of tracked tools relative to position-registered patient images and/or tracked anatomical structures during a planned surgical procedure. The computer platform 910 can display information on the display of FIGS. 3B and 3C and/or to one or more XR headsets 920. The computer platform 910, when used with a surgical robot, can be configured to communicate with the computer subsystem 820 and other subsystems of FIG. 8 to control movement of the end effector 26. For example, as will be explained below the computer platform 910 can generate a graphical representation of a patient's anatomical structure, surgical tool, user's hand, etc. with a displayed size, shape, color, and/or pose that is controlled based on the determined pose(s) of one or more the tracked DRAs, and which the graphical representation that is displayed can be dynamically modified to track changes in the determined poses over time.

Motion control subsystem 840 may be configured to physically move vertical column 16, upper arm 18, lower arm 20, or rotate end effector coupler 22. The physical movement may be conducted through the use of one or more motors 850-854. For example, motor 850 may be configured to vertically lift or lower vertical column 16. Motor 851 may be configured to laterally move upper arm 18 around a point of engagement with vertical column 16 as shown in FIG. 2. Motor 852 may be configured to laterally move lower arm 20 around a point of engagement with upper arm 18 as shown in FIG. 2. Motors 853 and 854 may be configured to move end effector coupler 22 to provide translational movement and rotation along in about three-dimensional axes. The computer platform 910 shown in FIG. 9 can provide control input to the controller 846 that guides movement of the end effector coupler 22 to position a passive end effector, which is connected thereto, with a planned pose (i.e., location and angular orientation relative to defined 3D orthogonal reference axes) relative to an anatomical structure that is to be operated on during a planned surgical procedure. Motion control subsystem 840 may be configured to measure position of the end effector coupler 22 and/or the end effector 26 using integrated position sensors (e.g. encoders).

Figure 9:
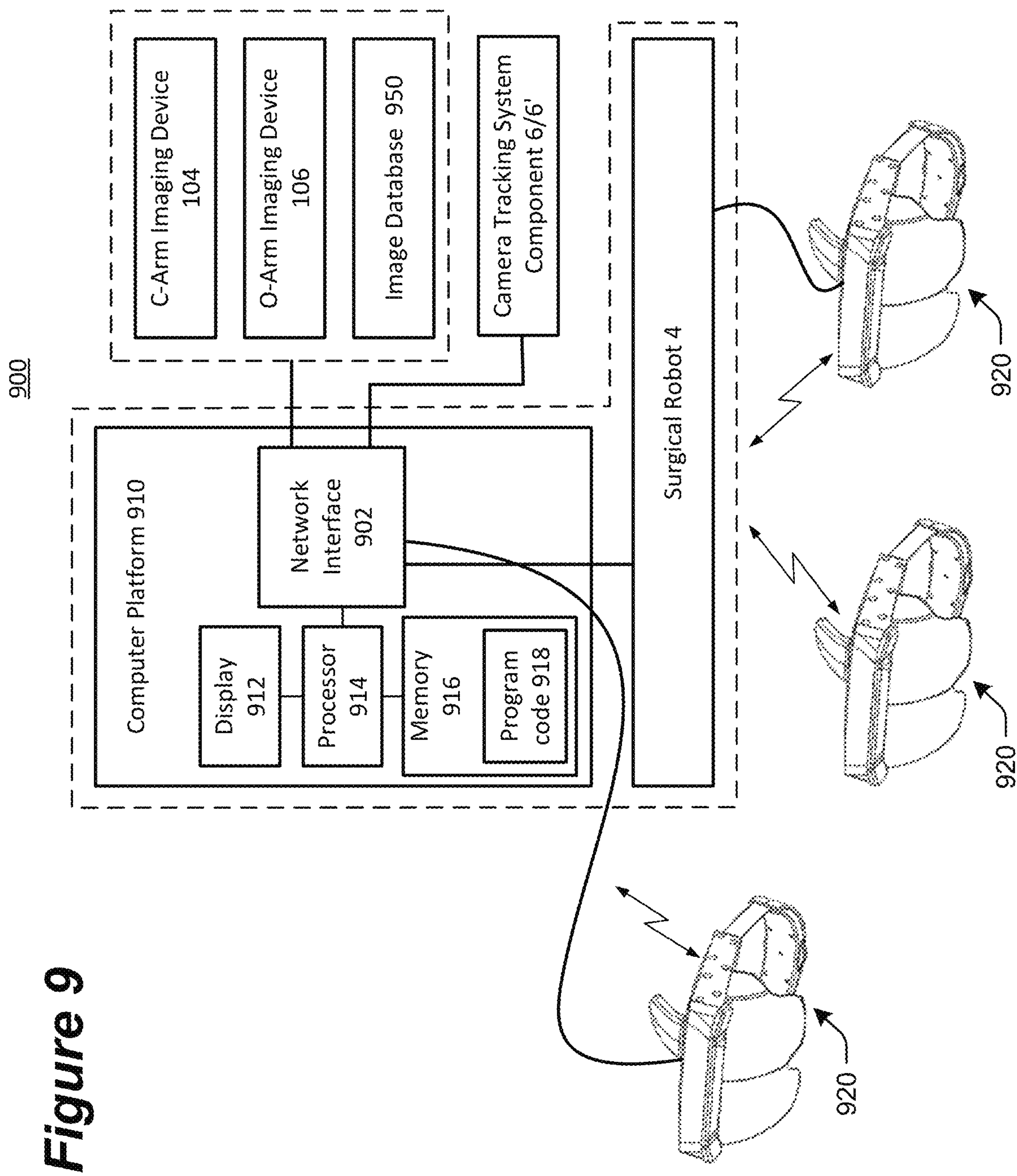
FIG. 9 illustrates a block diagram of components of a surgical system that includes imaging devices connected to a computer platform which can be operationally connected to a camera tracking system and/or surgical robot according to some embodiments of the present disclosure.

FIG. 9 illustrates a block diagram of components of a surgical system that includes imaging devices (e.g., C-Arm 104, O-Arm 106, etc.) connected to a computer platform 910 which can be operationally connected to a camera tracking system component 6 (FIG. 3A) or 6' (FIGS. 3B, 3C) and/or to surgical robot 4 according to some embodiments of the present disclosure. Alternatively, at least some operations disclosed herein as being performed by the computer platform 910 may additionally or alternatively be performed by components of a surgical system.

Referring to FIG. 9, the computer platform 910 includes a display 912, at least one processor circuit 914 (also referred to as a processor for brevity), at least one memory circuit 916 (also referred to as a memory for brevity) containing computer readable program code 918, and at least one network interface 902 (also referred to as a network interface for brevity). The display 912 may be part of an XR headset 920 in accordance with some embodiments of the present disclosure. The network interface 902 can be configured to connect to a C-Arm imaging device 104 in FIG. 10, an O-Arm imaging device 106 in FIG. 11, another medical imaging device, an image database 950 containing patient medical images, components of the surgical robot 4, and/or other electronic equipment.

When used with a surgical robot 4, the display 912 may correspond to the display 34 of FIG. 2 and/or the tablet 890 of FIG. 8 and/or the XR headset 920 that is operatively connected to the surgical robot 4, the network interface 902 may correspond to the platform network interface 812 of FIG. 8, and the processor 914 may correspond to the computer 822 of FIG. 8. The network interface 902 of the XR headset 920 may be configured to communicate through a wired network, e.g., thin wire ethernet, and/or through wireless RF transceiver link according to one or more wireless communication protocols, e.g., WLAN, 3GPP 4G and/or 5G (New Radio) cellular communication standards, etc.

The processor 914 may include one or more data processing circuits, such as a general purpose and/or special purpose processor, e.g., microprocessor and/or digital signal processor. The processor 914 is configured to execute the computer readable program code 918 in the memory 916 to perform operations, which may include some or all of the operations described herein as being performed for surgery planning, navigated surgery, and/or robotic surgery.

The computer platform 910 can be configured to provide surgery planning functionality. The processor 914 can operate to display on the display device 912 and/or on the XR headset 920 an image of an anatomical structure, e.g., vertebra, that is received from one of the imaging devices 104 and 106 and/or from the image database 950 through the network interface 920. The processor 914 receives an operator's definition of where the anatomical structure shown in one or more images is to have a surgical procedure, e.g., screw placement, such as by the operator touch selecting locations on the display 912 for planned procedures or using a mouse-based cursor to define locations for planned procedures. When the image is displayed in the XR headset 920, the XR headset can be configured to sense in gesture-based commands formed by the wearer and/or sense voice based commands spoken by the wearer, which can be used to control selection among menu items and/or control how objects are displayed on the XR headset 920 as will be explained in further detail below.

The computer platform 910 can be configured to enable anatomy measurement, which can be particularly useful for knee surgery, like measurement of various angles determining center of hip, center of angles, natural landmarks (e.g. transepicondylar line, Whitesides line, posterior condylar line), etc. Some measurements can be automatic while some others can involve human input or assistance. The computer platform 910 may be configured to allow an operator to input a choice of the correct implant for a patient, including choice of size and alignment. The computer platform 910 may be configured to perform automatic or semi-automatic (involving human input) segmentation (image processing) for CT images or other medical images. The surgical plan for a patient may be stored in a cloud-based server, which may correspond to database 950, for retrieval by the surgical robot 4.

During orthopedic surgery, for example, a surgeon may choose which cut to make (e.g. posterior femur, proximal tibia etc.) using a computer screen (e.g. touchscreen) or extended reality (XR) interaction (e.g., hand gesture based commands and/or voice based commands) via, e.g., the XR headset 920. The computer platform 910 can generate navigation information which provides visual guidance to the surgeon for performing the surgical procedure. When used with the surgical robot 4, the computer platform 910 can provide guidance that allows the surgical robot 4 to automatically move the end effector 26 to a target pose so that the surgical tool is aligned with a target location to perform the surgical procedure on an anatomical structure.

In some embodiments, the surgical system 900 can use two DRAs to track patient anatomy position, such as one connected to patient tibia and one connected to patient femur. The system 900 may use standard navigated instruments for the registration and checks (e.g. a pointer similar to the one used in Globus ExcelsiusGPS system for spine surgery).

A particularly challenging task in navigated surgery is how to plan the position of an implant in spine, knee, and other anatomical structures where surgeons struggle to perform the task on a computer screen which is a 2D representation of the 3D anatomical structure. The system 900 could address this problem by using the XR headset 920 to display a three-dimensional (3D) computer generated representations of the anatomical structure and a candidate implant device. The computer generated representations are scaled and posed relative to each other on the display screen under guidance of the computer platform 910 and which can be manipulated by a surgeon while viewed through the XR headset 920. A surgeon may, for example, manipulate the displayed computer-generated representations of the anatomical structure, the implant, a surgical tool, etc., using hand gesture based commands and/or voice based commands that are sensed by the XR headset 920.

For example, a surgeon can view a displayed virtual handle on a virtual implant, and can manipulate (e.g., grab and move) the virtual handle to move the virtual implant to a desired pose and adjust a planned implant placement relative to a graphical representation of an anatomical structure. Afterward, during surgery, the computer platform 910 could display navigation information through the XR headset 920 that facilitates the surgeon's ability to more accurately follow the surgical plan to insert the implant and/or to perform another surgical procedure on the anatomical structure. When the surgical procedure involves bone removal, the progress of bone removal, e.g., depth of cut, can be displayed in real-time through the XR headset 920. Other features that may be displayed through the XR headset 920 can include, without limitation, gap or ligament balance along a range of joint motion, contact line on the implant along the range of joint motion, ligament tension and/or laxity through color or other graphical renderings, etc.

The computer platform 910, in some embodiments, can allow planning for use of standard surgical tools and/or implants, e.g., posterior stabilized implants and cruciate retaining implants, cemented and cementless implants, revision systems for surgeries related to, for example, total or partial knee and/or hip replacement and/or trauma.

Figure 10:
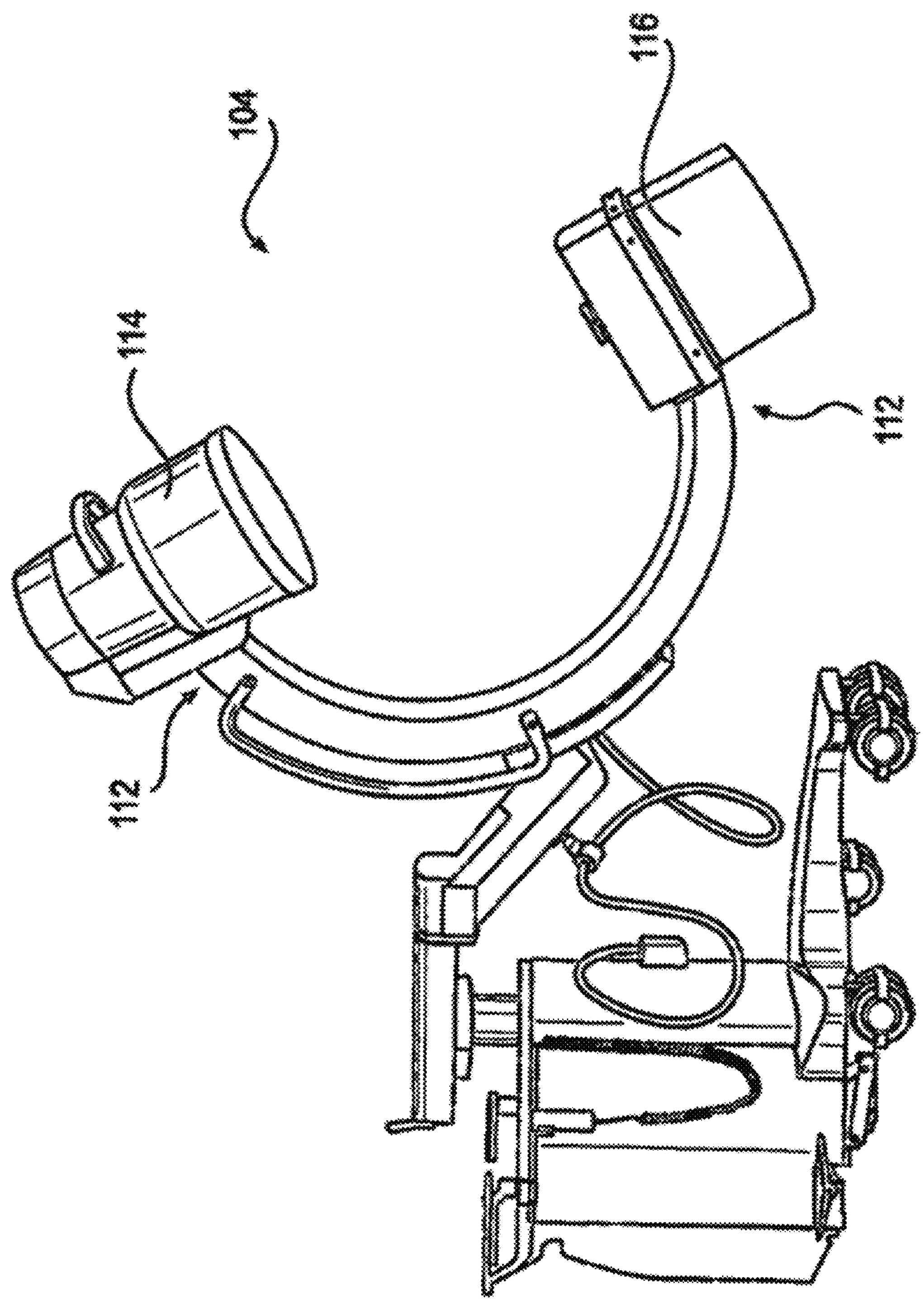
FIG. 10 illustrates an embodiment of a C-Arm imaging device that can be used in combination with the surgical robot in accordance with some embodiments of the present disclosure.
Figure 11:
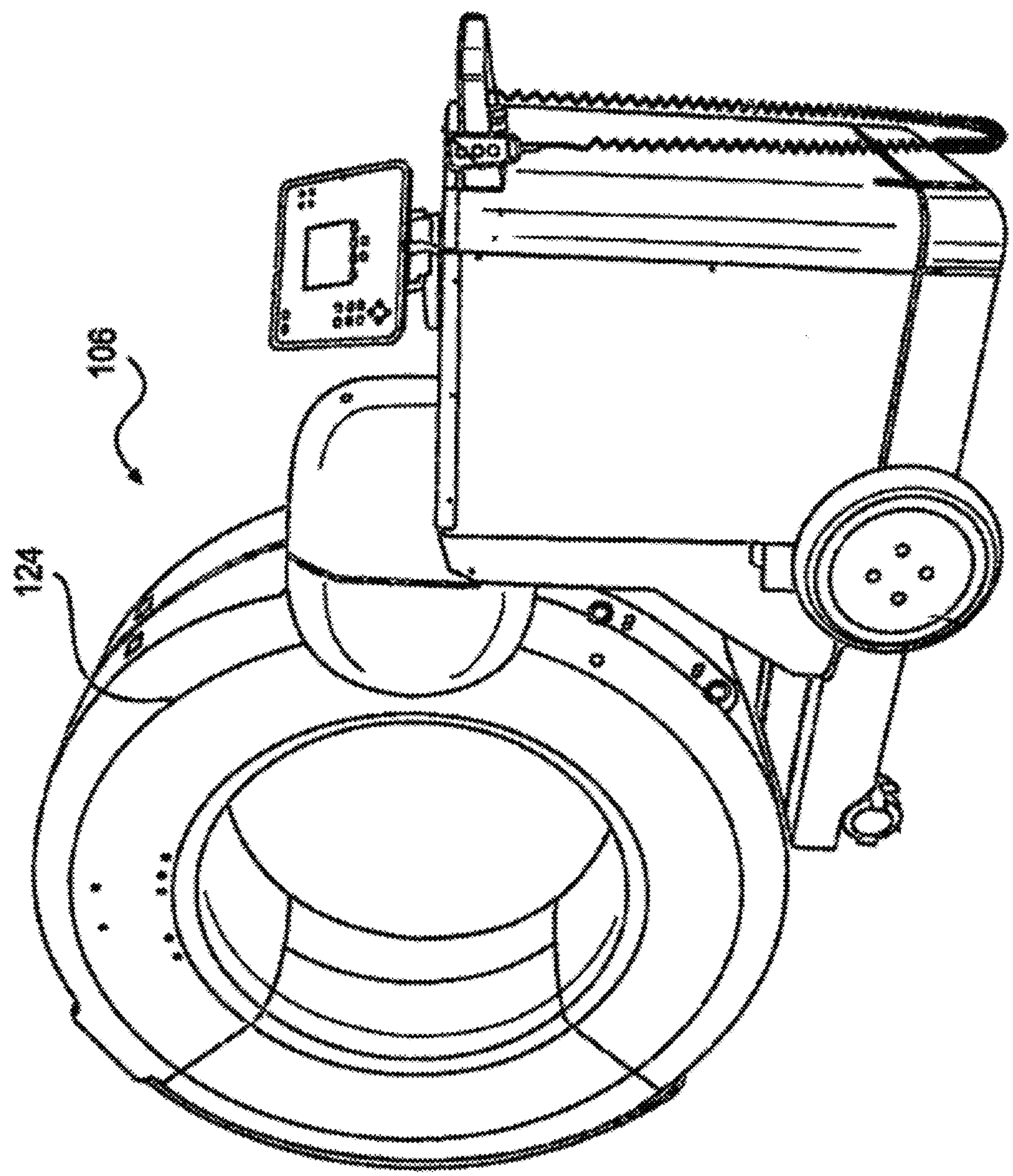
FIG. 11 illustrates an embodiment of an O-Arm imaging device that can be used in combination with the surgical robot in accordance with some embodiments of the present disclosure.

An automated imaging system can be used in conjunction with the computer platform 910 to acquire pre-operative, intra-operative, post-operative, and/or real-time image data of an anatomical structure. Example automated imaging systems are illustrated in FIGS. 10 and 11. In some embodiments, the automated imaging system is a C-arm 104 (FIG. 10) imaging device or an O-arm® 106 (FIG. 11). (O-arm® is copyrighted by Medtronic Navigation, Inc. having a place of business in Louisville, Colo., USA). It may be desirable to take x-rays of a patient from a number of different positions, without the need for frequent manual repositioning of the patient which may be required in an x-ray system. C-arm 104 x-ray diagnostic equipment may solve the problems of frequent manual repositioning and may be well known in the medical art of surgical and other interventional procedures. As illustrated in FIG. 10, a C-arm includes an elongated C-shaped member terminating in opposing distal ends 112 of the "C" shape. C-shaped member is attached to an x-ray source 114 and an image receptor 116. The space within C-arm 104 of the arm provides room for the physician to attend to the patient substantially free of interference from the x-ray support structure.

The C-arm is mounted to enable rotational movement of the arm in two degrees of freedom, (i.e. about two perpendicular axes in a spherical motion). C-arm is slidably mounted to an x-ray support structure, which allows orbiting rotational movement of the C-arm about its center of curvature, which may permit selective orientation of x-ray source 114 and image receptor 116 vertically and/or horizontally. The C-arm may also be laterally rotatable, (i.e. in a perpendicular direction relative to the orbiting direction to enable selectively adjustable positioning of x-ray source 114 and image receptor 116 relative to both the width and length of the patient). Spherically rotational aspects of the C-arm apparatus allow physicians to take x-rays of the patient at an optimal angle as determined with respect to the particular anatomical condition being imaged.

The O-arm® 106 illustrated in FIG. 11 includes a gantry housing 124 which may enclose an image capturing portion, not illustrated. The image capturing portion includes an x-ray source and/or emission portion and an x-ray receiving and/or image receiving portion, which may be disposed about one hundred and eighty degrees from each other and mounted on a rotor (not illustrated) relative to a track of the image capturing portion. The image capturing portion may be operable to rotate three hundred and sixty degrees during image acquisition. The image capturing portion may rotate around a central point and/or axis, allowing image data of the patient to be acquired from multiple directions or in multiple planes.

The O-arm® 106 with the gantry housing 124 has a central opening for positioning around an object to be imaged, a source of radiation that is rotatable around the interior of gantry housing 124, which may be adapted to project radiation from a plurality of different projection angles. A detector system is adapted to detect the radiation at each projection angle to acquire object images from multiple projection planes in a quasi-simultaneous manner. The gantry may be attached to a support structure O-arm® support structure, such as a wheeled mobile cart with wheels, in a cantilevered fashion. A positioning unit translates and/or tilts the gantry to a planned position and orientation, preferably under control of a computerized motion control system. The gantry may include a source and detector disposed opposite one another on the gantry. The source and detector may be secured to a motorized rotor, which may rotate the source and detector around the interior of the gantry in coordination with one another. The source may be pulsed at multiple positions and orientations over a partial and/or full three hundred and sixty degree rotation for multi-planar imaging of a targeted object located inside the gantry. The gantry may further comprise a rail and bearing system for guiding the rotor as it rotates, which may carry the source and detector. Both and/or either O-arm® 106 and C-arm 104 may be used as automated imaging system to scan a patient and send information to the surgical system 2.

Images captured by an imaging system can be displayed on the XR headset 920 and/or another display device of the computer platform 910, the surgical robot 4, and/or another component of the surgical system 900. The XR headset 920 may be connected to one or more of the imaging devices 104 and/or 106 and/or to the image database 950, e.g., via the computer platform 910, to display images therefrom. A user may provide control inputs through the XR headset 920, e.g., gesture and/or voice based commands, to control operation of one or more of the imaging devices 104 and/or 106 and/or the image database 950.

Figure 12:
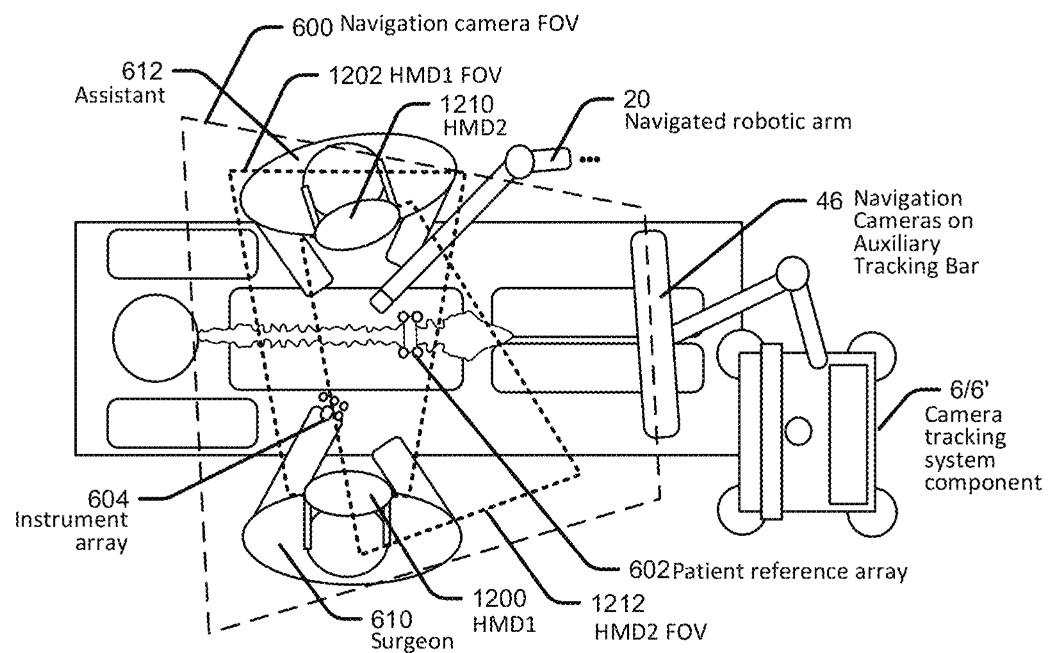
FIG. 12 illustrates a block diagram view of the components of a surgical system that includes a pair of XR headsets and an auxiliary tracking bar which operate in accordance with some embodiments of the present disclosure.
Figure 13:
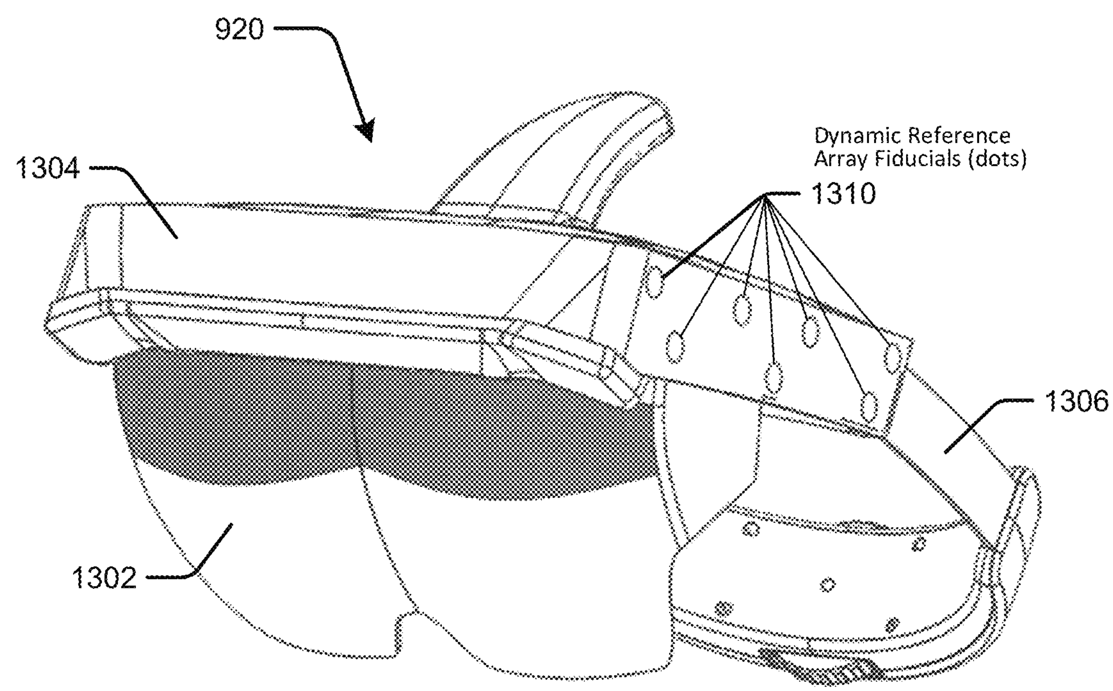
FIG. 13 illustrates an XR headset which is configured in accordance with some embodiments of the present disclosure.

FIG. 12 illustrates a block diagram view of the components of a surgical system that include a pair of XR headsets 1200 and 1210 (head-mounted displays HMD1 and HMD2), which may correspond to the XR headset 920 shown in FIG. 13 and operate in accordance with some embodiments of the present disclosure.

Referring to the example scenario of FIG. 12, the assistant 612 and surgeon 610 are both wearing the XR headsets 1210 and 1210, respectively. It is optional for the assistant 612 to wear the XR headset 1210. The XR headsets 1200 and 1210 are configured to provide an interactive environment through which the wearers can view and interact with information related to a surgical procedure as will be described further below. This interactive XR based environment may eliminate a need for the tech personnel 614 to be present in the operating room and may eliminate a need for use of the display 34 shown in FIG. 6. Each XR headset 1200 and 1210 can include one or more cameras that are be configured to provide an additional source of tracking of DRAs or other reference arrays attached to instruments, an anatomical structure, the end effector 26, and/or other equipment. In the example of FIG. 12, XR headset 1200 has a field-of-view (FOV) 1202 for tracking DRAs and other objects, XR headset 1210 has a FOV 1212 partially overlapping FOV 1202 for tracking DRAs and other objects, and the navigation cameras 46 has another FOV 600 partially overlapping FOVs 1202 and 1212 for tracking DRAs and other objects.

If one or more cameras is obstructed from viewing a DRA attached to a tracked object, e.g., a surgical instrument, but the DRA is in view of one or more other cameras the tracking subsystem 830 and/or navigation controller 828 can continue to track the object seamlessly without loss of navigation. Additionally, if there is partial occlusion of the DRA from the perspective of one camera, but the entire DRA is visible via multiple camera sources, the tracking inputs of the cameras can be merged to continue navigation of the DRA. One of the XR headsets and/or the navigation cameras 46 may view and track the DRA on another one of the XR headsets to enable the computer platform 910 (FIGS. 9 and 14), the tracking subsystem 830, and/or another computing component to determine the pose of the DRA relative to one or more defined coordinate systems, e.g., of the XR headsets 1200/1210, the navigation cameras 46, and/or another coordinate system defined for the patient, table, and/or room.

The XR headsets 1200 and 1210 can be operatively connected to view video, pictures, and/or other information received from and/or to provide commands that control various equipment in the surgical room, including but not limited to neuromonitoring, microscopes, video cameras, and anesthesia systems. Data from the various equipment may be processed and displayed within the headset, for example the display of patient vitals or the microscope feed.

Example XR Headset Components and Integration to Navigated Surgery, Surgical Robots, and Other Equipment FIG. 13 illustrates an XR headset 920 which is configured in accordance with some embodiments of the present disclosure. The XR headset includes a headband 1306 configured to secure the XR headset to a wearer's head, an electronic component enclosure 1304 supported by the headband 1306, and a display screen 1302 that extends laterally across and downward from the electronic component enclosure 1304. The display screen 1302 may be a see-through LCD display device or a semi-reflective lens that reflects images projected by a display device toward the wearer's eyes. A set of DRA fiducials, e.g., dots are painted or attached in a spaced apart known arranged on one or both sides of the headset. The DRA on the headset enables the navigation cameras on the auxiliary tracking bar to track pose of the headset 920 and/or enables another XR headset to track pose of the headset 920.

The display screen 1302 operates as a see-through display screen, also referred to as a combiner, that reflects light from display panels of a display device toward the user's eyes. The display panels can be located between the electronic component enclosure and the user's head, and angled to project virtual content toward the display screen 1302 for reflection toward the user's eyes. The display screen 1302 is semi-transparent and semi-reflective allowing the user to see reflected virtual content superimposed on the user's view of a real-world scene. The display screen 1302 may have different opacity regions, such as the illustrated upper laterally band which has a higher opacity than the lower laterally band. Opacity of the display screen 1302 may be electronically controlled to regulate how much light from the real-world scene passes through to the user's eyes. A high opacity configuration of the display screen 1302 results in high-contrast virtual images overlaid on a dim view of the real-world scene. A low opacity configuration of the display screen 1302 can result in more faint virtual images overlaid on a clearer view of the real-world scene. The opacity may be controlled by applying an opaque material on a surface of the display screen 1302.

Figure 14:
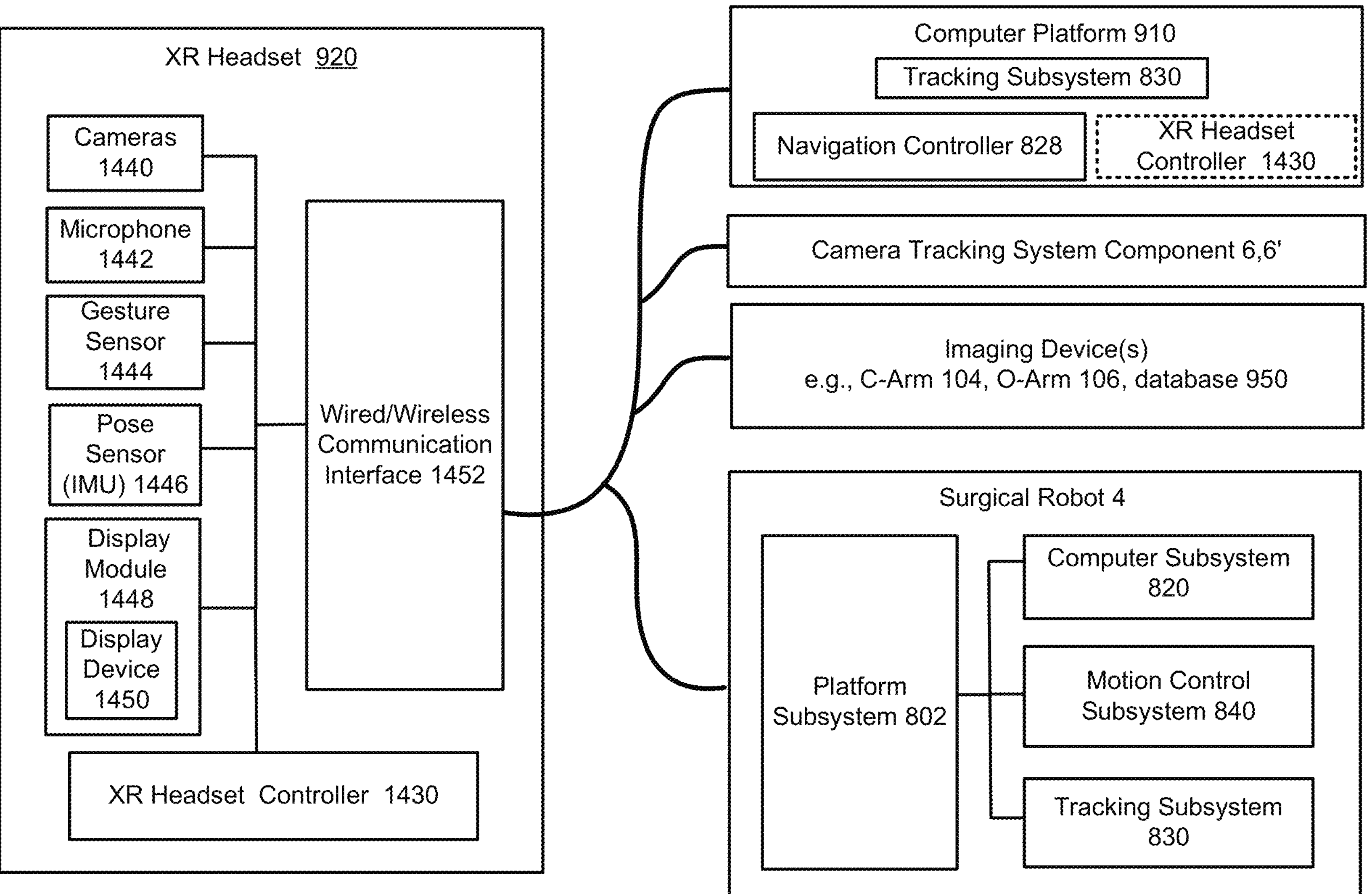
FIG. 14 illustrates electrical components of the XR headset that can be operatively connected to a computer platform, imaging device(s), and/or a surgical robot in accordance with some embodiments of the present disclosure.

According to some embodiments the surgical system includes an XR headset 920 and an XR headset controller, e.g., controller 1430 in FIG. 14. The XR headset 920 is configured to be worn by a user during a surgical procedure and has a see-through display screen 1302 that is configured to display an XR image and to allow at least a portion of a real-world scene to pass therethrough for viewing by the user. The XR headset 920 also includes an opacity filter positioned between at least one of the user's eyes and the real-world scene when the see-through display screen 1302 is viewed by the user. The opacity filter is configured to provide opaqueness to light from the real-world scene. The XR headset controller is configured to communicate with a navigation controller, e.g., controller(s) 828A, 828B, and/or 828C in FIG. 14, to receive navigation information from the navigation controller which provides guidance to the user during the surgical procedure on an anatomical structure, and is further configured to generate the XR image based on the navigation information for display on the see-through display screen 1302.

Opacity of the display screen 1302 may be configured as a gradient having a more continuously changing opacity with distance downward from a top portion of the display screen 1302. The gradient's darkest point can be located at the top portion of the display screen 1302, and gradually becoming less opaque further down on the display screen 1302 until the opacity is transparent or not present. In an example further embodiment, the gradient can change from about 90% opacity to entirely transparent approximately at the mid-eye level of the display screen 1302. With the headset properly calibrated and positioned, the mid-eye level can correspond to the point where the user would look straight out, and the end of the gradient would be located at the "horizon" line of the eye. The darker portion of the gradient will allow crisp, clear visuals of the virtual content and help to block the intrusive brightness of the overhead operating room lights.

Using an opacity filter in this manner enables the XR headset 920 to provide virtual reality (VR) capabilities, by substantially or entirely blocking light from the real-world scene, along an upper portion of the display screen 1302 and to provide AR capabilities along a middle or lower portion of the display screen 1302. This allows the user to have the semi-translucence of AR where needed and allowing clear optics of the patient anatomy during procedures. Configuring the display screen 1302 as a gradient instead of as a more constant opacity band can enable the wearer to experience a more natural transition between a more VR type view to a more AR type view without experiencing abrupt changes in brightness of the real-world scene and depth of view that may otherwise strain the eyes such as during more rapid shifting between upward and downward views.

The display panels and display screen 1302 can be configured to provide a wide field of view see-through XR display system. In one example configuration they provide an 80° diagonal field-of-view (FOV) with 55° of vertical coverage for a user to view virtual content. Other diagonal FOV angles and vertical coverage angles can be provided through different size display panels, different curvature lens, and/or different distances and angular orientations between the display panels and curved display screen 1302.

FIG. 14 illustrates electrical components of the XR headset 920 that can be operatively connected to the computer platform 910, to one or more of the imaging devices, such as the C-arm imaging device 104, the O-arm imaging device 106, and/or the image database 950, and/or to the surgical robot 800 in accordance with various embodiments of the present disclosure.

The XR headset 920 provides an improved human interface for performing navigated surgical procedures. The XR headset 920 can be configured to provide functionalities, e.g., via the computer platform 910, that include without limitation any one or more of: identification of hand gesture based commands and/or voice based commands, display XR graphical objects on a display device 1450. The display device 1450 may be a video projector, flat panel display, etc., which projects the displayed XR graphical objects on the display screen 1302. The user can view the XR graphical objects as an overlay anchored to particular real-world objects viewed through the display screen 1302 (FIG. 13). The XR headset 920 may additionally or alternatively be configured to display on the display screen 1450 video feeds from cameras mounted to one or more XR headsets 920 and other cameras.

Electrical components of the XR headset 920 can include a plurality of cameras 1440, a microphone 1442, a gesture sensor 1444, a pose sensor (e.g., inertial measurement unit (IMU)) 1446, a display module 1448 containing the display device 1450, and a wireless/wired communication interface 1452. As will be explained below, the cameras 1440 of the XR headset may be visible light capturing cameras, near infrared capturing cameras, or a combination of both.

The cameras 1440 may be configured operate as the gesture sensor 1444 by capturing for identification user hand gestures performed within the field of view of the camera(s) 1440. Alternatively the gesture sensor 1444 may be a proximity sensor and/or a touch sensor that senses hand gestures performed proximately to the gesture sensor 1444 and/or senses physical contact, e.g. tapping on the sensor or the enclosure 1304. The pose sensor 1446, e.g., IMU, may include a multi-axis accelerometer, a tilt sensor, and/or another sensor that can sense rotation and/or acceleration of the XR headset 920 along one or more defined coordinate axes. Some or all of these electrical components may be contained in the component enclosure 1304 or may be contained in another enclosure configured to be worn elsewhere, such as on the hip or shoulder.

As explained above, the surgical system 2 includes a camera tracking system component 6/6' and a tracking subsystem 830 which may be part of the computer platform 910. The surgical system may include imaging devices (e.g., C-arm 104, O-arm 106, and/or image database 950) and/or a surgical robot 4. The tracking subsystem 830 is configured to determine a pose of DRAs attached to an anatomical structure, an end effector, a surgical tool, etc. A navigation controller 828 is configured to determine a target pose for the surgical tool relative to an anatomical structure based on a surgical plan, e.g., from a surgical planning function performed by the computer platform 910 of FIG. 9, defining where a surgical procedure is to be performed using the surgical tool on the anatomical structure and based on a pose of the anatomical structure determined by the tracking subsystem 830. The navigation controller 828 may be further configured to generate steering information based on the target pose for the surgical tool, the pose of the anatomical structure, and the pose of the surgical tool and/or the end effector, where the steering information indicates where the surgical tool and/or the end effector of a surgical robot should be moved to perform the surgical plan.

The electrical components of the XR headset 920 can be operatively connected to the electrical components of the computer platform 910 through a wired/wireless interface 1452. The electrical components of the XR headset 920 may be operatively connected, e.g., through the computer platform 910 or directly connected, to various imaging devices, e.g., the C-arm imaging device 104, the I/O-arm imaging device 106, the image database 950, and/or to other medical equipment through the wired/wireless interface 1452.

The surgical system 2 further includes at least one XR headset controller 1430 (also referred to as "XR headset controller" for brevity) that may reside in the XR headset 920, the computer platform 910, and/or in another system component connected via wired cables and/or wireless communication links. Various functionality is provided by software executed by the XR headset controller 1430. The XR headset controller 1430 is configured to receive navigation information from the navigation controller 828 which provides guidance to the user during the surgical procedure on an anatomical structure, and is configured to generate an XR image based on the navigation information for display on the display device 1450 for projection on the see-through display screen 1302.

The configuration of the display device 1450 relative to the display screen (also referred to as "see-through display screen") 1302 is configured to display XR images in a manner such that when the user wearing the XR headset 920 looks through the display screen 1302 the XR images appear to be in the real world. The display screen 1302 can be positioned by the headband 1306 in front of the user's eyes.

The XR headset controller 1430 can be within a housing that is configured to be worn on a user's head or elsewhere on the user's body while viewing the display screen 1302 or may be remotely located from the user viewing the display screen 1302 while being communicatively connected to the display screen 1302. The XR headset controller 1430 can be configured to operationally process signaling from the cameras 1440, the microphone 142, and/or the pose sensor 1446, and is connected to display XR images on the display device 1450 for user viewing on the display screen 1302. Thus, the XR headset controller 1430 illustrated as a circuit block within the XR headset 920 is to be understood as being operationally connected to other illustrated components of the XR headset 920 but not necessarily residing within a common housing (e.g., the electronic component enclosure 1304 of FIG. 13) or being otherwise transportable by the user. For example, the XR headset controller 1430 may reside within the computer platform 910 which, in turn, may reside within a housing of the computer tracking system component 6' shown in FIGS. 3B and 3C.

Example XR Headset Component Optical Arrangement

FIG. 13 illustrates a block diagram showing arrange of optical components of the XR headset 920 in accordance with some embodiments of the present disclosure. Referring to FIGS. 13 and 14, the display device 1450 is configured to display XR images generated by the XR headset controller 1430, light from which is projected as XR images 1450 toward the display screen 1302. The display screen 1302 is configured to combine light of the XR images 1450 and light from the real-world scene 1502 into a combined augmented view 1504 that is directed to the user's eye(s) 1510. The display screen 1302 configured in this manner operates as a see-through display screen. The XR headset 920 can include any plural number of navigation cameras 1440. The cameras 1440 may be visible light capturing cameras, near infrared capturing cameras, or a combination of both.

Example User Views through the XR Headset

The XR headset operations can display both 2D images and 3D models on the display screen 1302. The 2D images may preferably be displayed in a more opaque band of the display screen 1302 (upper band) and the 3D model may be more preferably displayed in the more transparent band of the display screen 1302, otherwise known as the environmental region (bottom band). Below the lower band where the display screen 1302 ends the wearer has an unobstructed view of the surgical room. It is noted that where XR content is display on the display screen 1302 may be fluidic. It is possible that where the 3D content is displayed moves to the opaque band depending on the position of the headset relative to the content, and where 2D content is displayed can be placed in the transparent band and stabilized to the real world. Additionally, the entire display screen 1302 may be darkened under electronic control to convert the headset into virtual reality for surgical planning or completely transparent during the medical procedure. As explained above, the XR headset 920 and associated operations not only support navigated procedures, but also can be performed in conjunction with robotically assisted procedures.

Figure 15:
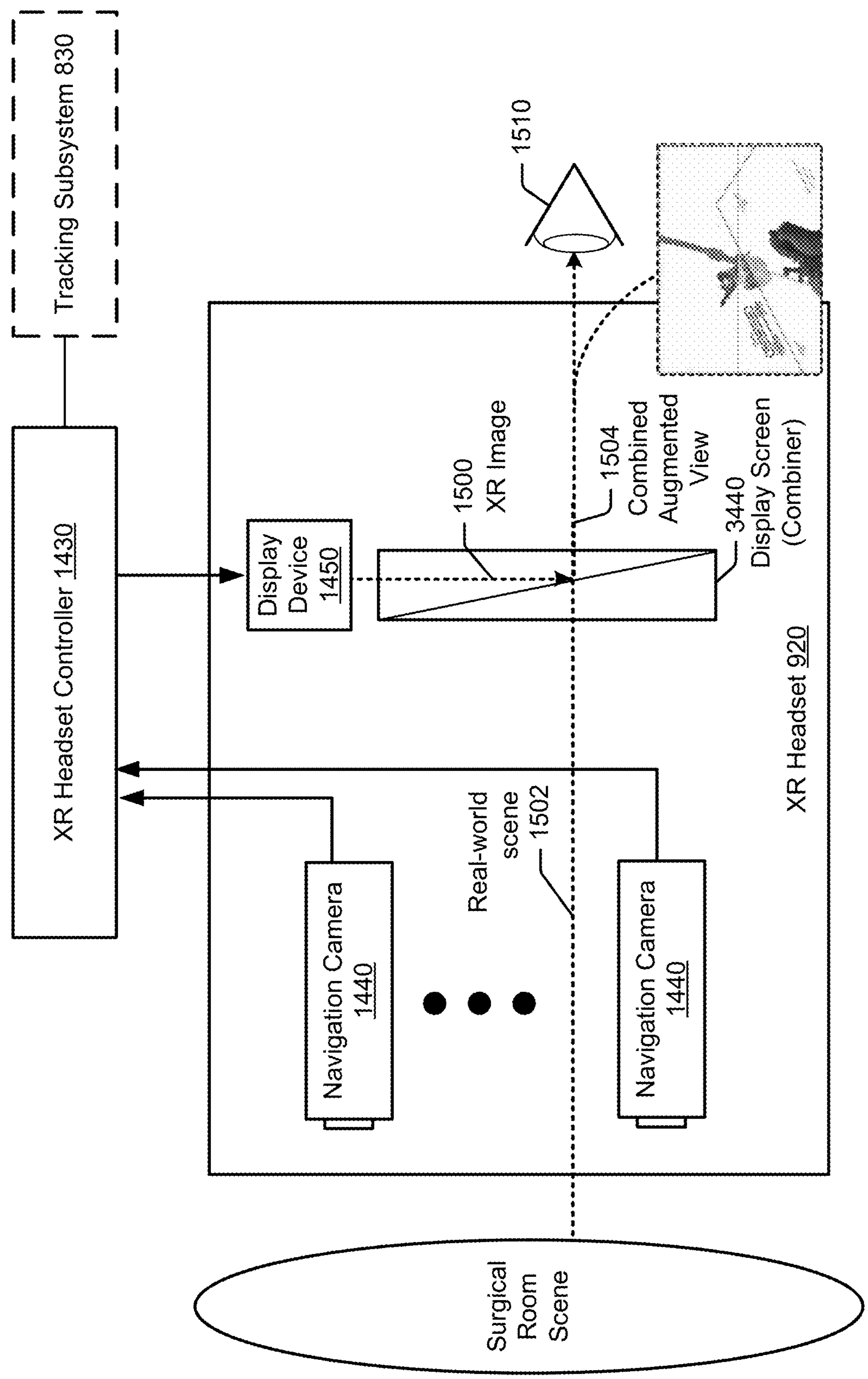
FIG. 15 illustrates a block diagram showing arrangement of optical components of the XR headset in accordance with some embodiments of the present disclosure.
Figure 16:
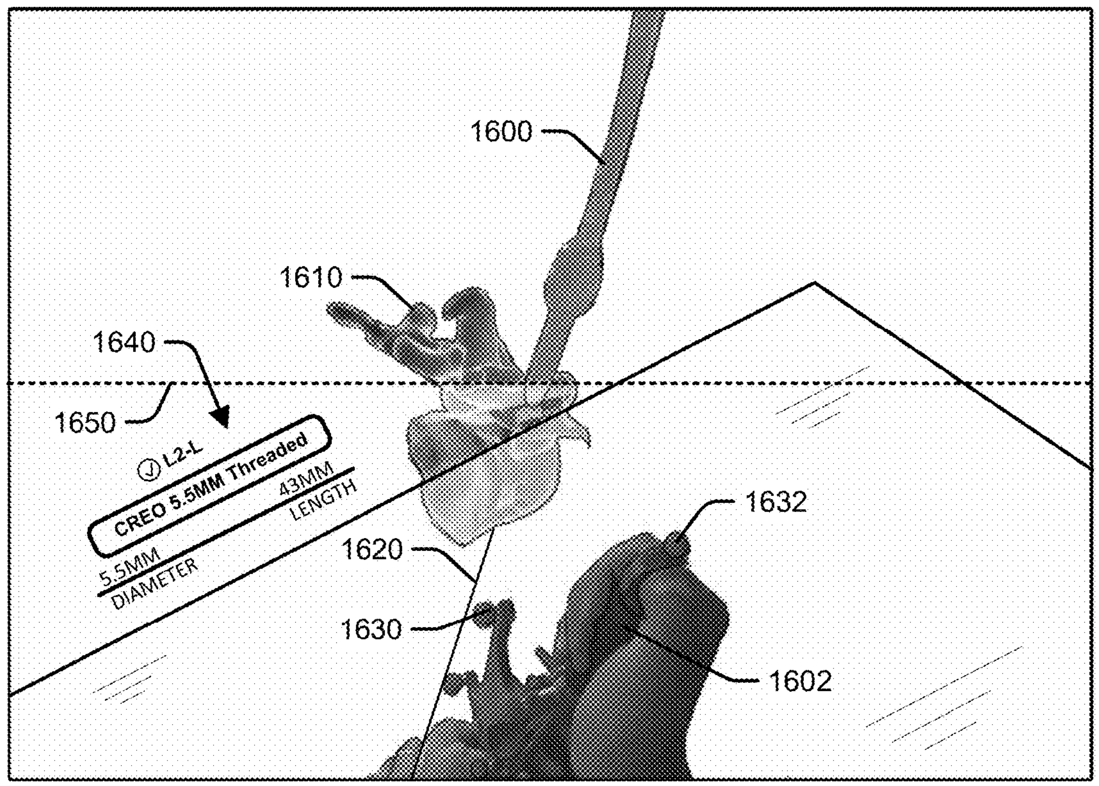
FIG. 16 illustrates an example view through the display screen of an XR headset for providing navigation assistance to manipulate a surgical tool during a medical procedure in accordance with some embodiments of the present disclosure.

FIG. 16 illustrates an example view through the display screen 1302 of the XR headset 920 for providing navigation assistance to a user who is manipulating a surgical tool 1602 during a medical procedure in accordance with some embodiments of the present disclosure. Referring to FIG. 16, when the surgical tool 1602 is brought in vicinity of a tracked anatomical structure so that dynamic reference arrays 1630 and 1632, connected to the surgical tool 1602, become within the field of view of the cameras 1440 (FIG. 15) and/or 46 (FIG. 6), a graphical representation 1600 of the tool can be displayed in 2D and/or 3D images in relation to a graphical representation 1610 of the anatomical structure. The user can use the viewed graphical representations to adjust a trajectory 1620 of the surgical tool 1602, which can be illustrated as extending from the graphical representation 2000 of the tool through the graphical representation 1610 of the anatomical structure. The XR headset 920 may also display textual information and other objects 1640. The dashed line 1650 extending across the viewed display screen represents an example division between different opacity level upper and lower bands.

Other types of XR images (virtual content) that can be displayed on the display screen 1302 can include, but are not limited to any one or more of:

1) 2D Axial, Sagittal and/or Coronal views of patient anatomy;
2) overlay of planned vs currently tracked tool and surgical implant locations;
3) gallery of preoperative images;
4) video feeds from microscopes and other similar systems or remote video conferencing;
5) options and configuration settings and buttons;
6) floating 3D models of patient anatomy with surgical planning information;
7) real-time tracking of surgical instruments relative to floating patient anatomy;
8) augmented overlay of patient anatomy with instructions and guidance; and
9) augmented overlay of surgical equipment.

Example Configuration of Cameras for Tracking System Component

Figure 17:
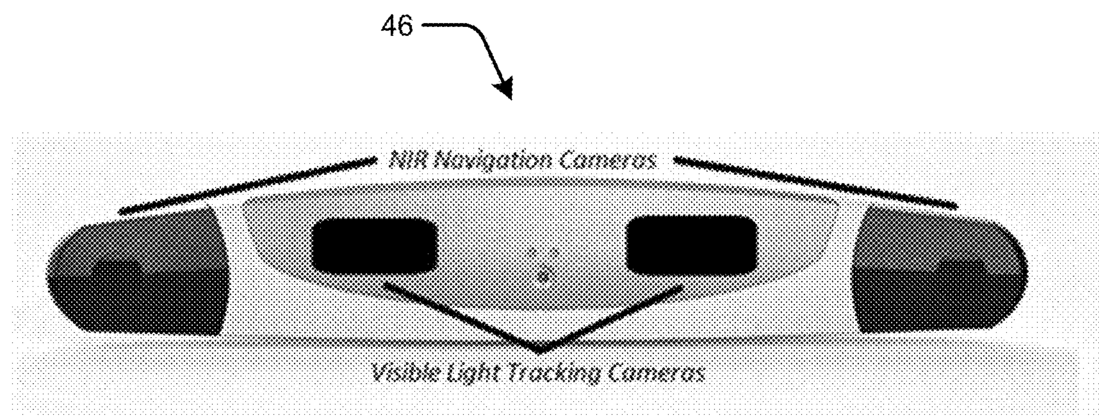
FIG. 17 illustrates an example configuration of an auxiliary tracking bar having two pairs of stereo cameras configured in accordance with some embodiments of the present disclosure.

FIG. 17 illustrates example configuration of an auxiliary tracking bar 46 having two pairs of stereo navigation cameras configured in accordance with some embodiments of the present disclosure. The auxiliary tracking bar 46 is part of the camera tracking system component of FIGS. 3A, 3B, and 3C. The stereo navigation cameras include a stereo pair of spaced apart visible light capturing cameras and another stereo pair of spaced apart near infrared capturing cameras, in accordance with one embodiment. Alternatively, only one stereo pair of visible light capturing cameras or only one stereo pair of near infrared capture cameras can used in the auxiliary tracking bar 46. Any plural number of near infrared and/or visible light cameras can be used.

Pose Measurement Chaining

As explained above, navigated surgery can include computer vision tracking and determination of pose (e.g., position and orientation in a six degree-of-freedom coordinate system) of surgical instruments, such as by determining pose of attached DRAs that include spaced apart fiducials, e.g., disks or spheres, arranged in a known manner. The computer vision uses spaced apart navigation cameras, e.g., stereo cameras, that are configured to capture near infrared and/or visible light. In this scenario, there are three parameters jointly competing for optimization: (1) accuracy, (2) robustness, and (3) user ergonomics during a surgical procedure.

Some further aspects of the present disclosure are directed to computer operations that combine (chain) measured poses in ways that can improve optimization of one or more of the above three parameters by incorporating additional navigation cameras mounted to one or more XR headsets. As shown in FIG. 17, a stereo pair of visible light tracking cameras and another stereo pair of near infrared tracking navigation cameras can be attached to the auxiliary tracking bar of the camera tracking system component in accordance with some embodiments of the present disclosure. Operational algorithms are disclosed that analyze the pose of DRAs that are fully observed or partially observed (e.g., when less than all of the fiducials of a DRA are viewed by a pair of stereo cameras), and combine the observed poses or partial poses in ways that can improve accuracy, robustness, and/or ergonomics during navigated surgery.

As explained above, the XR headset may be configured to augment a real-world scene with computer generated XR images. The XR headset may be configured to provide an XR viewing environment by displaying the computer generated XR images on a see-through display screen that allows light from the real-world scene to pass therethrough for combined viewing by the user. Alternatively, the XR headset may be configured to provide a VR viewing environment by preventing or substantially preventing light from the real-world scene from being directly viewed by the user along the viewing path of the displayed XR images. An XR headset can be configured to provide both AR and VR viewing environments. In one embodiment, both AR and VR viewing environments are provided by lateral bands of substantially differing opacity arranged between the see-through display screen and the real-world scene, so that a VR viewing environment is provided for XR images aligned with a high opacity band and an AR viewing environment is provided for XR images aligned with the low opacity band. In another embodiment, both AR and VR viewing environments are provided by computer adjustable control of an opacity filter that variably constrains how much light from the real-world scene passes through a see-through display screen for combining with the XR images viewed by the user. Thus, the XR headset can also be referred to as an AR headset or a VR headset.

As was also explained above, the XR headset can include near infrared tracking cameras and/or visible light tracking cameras that are configured to track fiducials of DRAs connected to surgical instruments, patient anatomy, other XR headset(s), and/or a robotic end effector. Using near infrared tracking and/or visible light tracking on the XR headset provides additional tracking volume coverage beyond what cameras on a single auxiliary tracking bar can provide. Adding near infrared tracking cameras to the existing auxiliary tracking bar allows for the headset location to be tracked more robustly but less accurately than in visible light. Mechanically calibrating the visible and near infrared tracking coordinate systems enables the coordinate systems to be aligned sufficiently to perform 3D DRA fiducials triangulation operations using stereo matching to jointly identify pose of the DRA fiducials between the visible and near infrared tracking coordinate systems. Using both visible and near infrared tracking coordinate systems can enable any one or more of: (a) identifying tools that would not be identified using a single coordinate system; (b) increased pose tracking accuracy; (c) enabling a wider range of motion without losing tracking of surgical instruments, patient anatomy, and/or a robotic end effector; and (d) naturally track an XR headset in the same coordinate system as the navigated surgical instruments.

Figure 18:
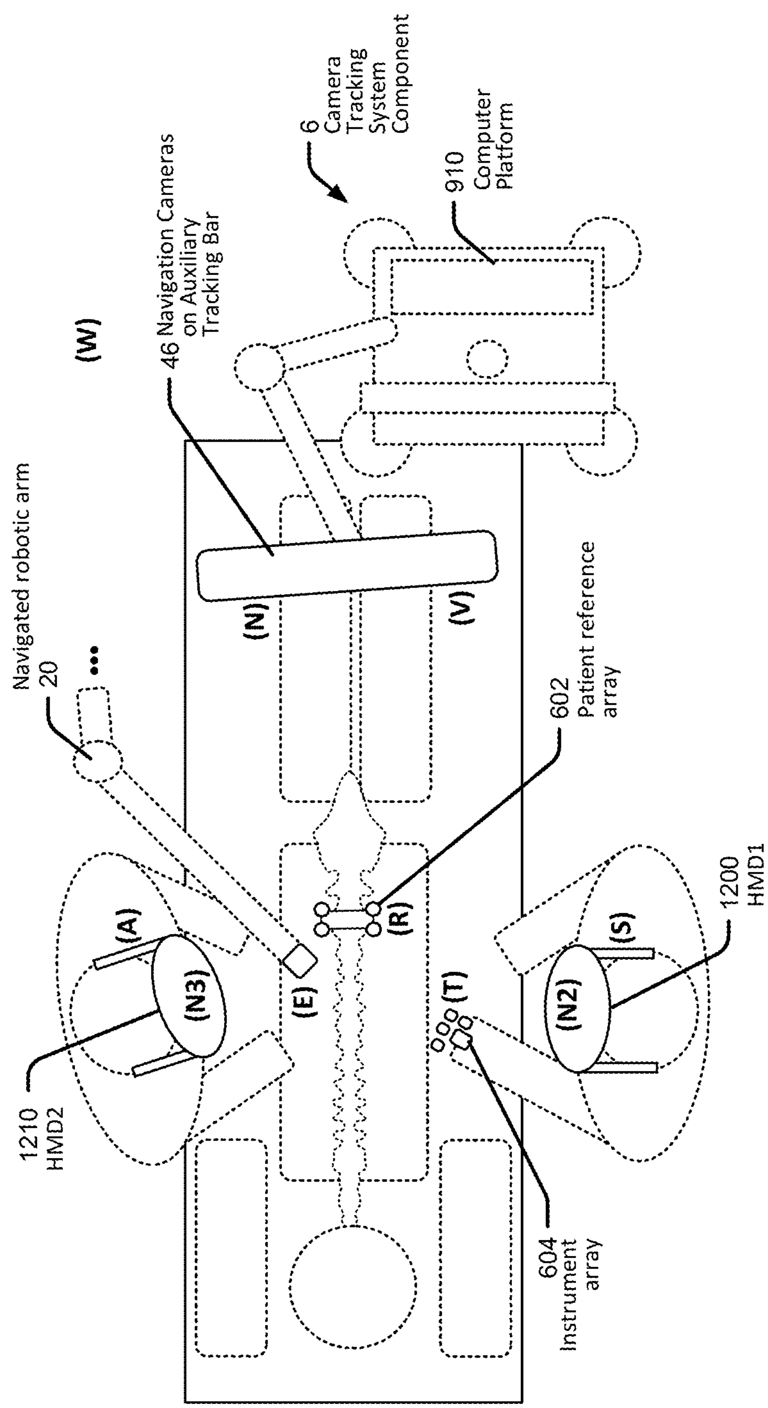
FIG. 18 illustrates a block diagram view of the components of a surgical system that includes navigation cameras in a pair of XR headsets and in an auxiliary tracking bar which collectively operate in accordance with some embodiments of the present disclosure.

FIG. 18 illustrates a block diagram view of the components of a surgical system that include navigation cameras in a pair of XR headsets 1200 and 1210 (head-mounted displays HMD1 and HMD2) and navigation cameras in a camera tracking bar in the camera tracking system component 6' which houses the computer platform 910. The computer platform 910 can include the tracking subsystem 830, the navigation controller 828, and the XR headset controller 1430 as was earlier shown in FIG. 14.

Referring to the surgical system of FIG. 18, a surgeon and an assistant are both wearing XR headsets HMD1 1200 and HMD2 1210, respectively, each if which includes navigation cameras that may be configured as shown in FIG. 13. It is optional for the assistant to wear the XR headset HMD2 1210.

The combination of XR headsets HMD1 1200 and HMD2 1210 and the navigation cameras 46 on the auxiliary tracking bar can, in operation with the computer platform 910, more robustly track the example objects of a patient reference array (R), robotic end effector (E), and surgical tool (T) or instrument. The overlapping views from different perspectives that are provided by the XR headsets HMD1 1200 and HMD2 1210 and the navigation cameras 46 on the auxiliary tracking bar are shown in FIG. 12.

Each of the items labeled in FIG. 18 represent a unique coordinate system. Descriptions of the coordinate system labels are as follows:

A=visible light coordinate system of second headset HMD2 1210;

N3=NIR coordinate system of second headset HMD2 1210;

S=visible light coordinate system of primary headset HMD1 1200;

N2=NIR coordinate system of the primary headset HMD1 1200;

N=NIR coordinate system of the auxiliary navigation bar 46;

V=visible light coordinate system of the auxiliary navigation bar 46;

R=NIR coordinate system of a patient reference fiducial array 602;

T=NIR coordinate system of a tracked tool 604;

E=NIR coordinate system of a tracked robot end effector on robotic arm 20; and W=Inertially navigated world coordinate system with stable gravity vector.

The spatial relationships of some of these labeled objects (and by extension, coordinate systems) can be measured and calibrated during the manufacturing process, when the equipment is installed in an operating room, and/or before a surgical procedure is to be performed. In the disclosed system, the following coordinate systems are calibrated: ${}^{S}T_{N2}$; ${}^{A}T_{N3}$; ${}^{V}T_{N}$, where the term "T" is defined as a six degree-of-freedom (6 DOF) homogeneous transformation between the two indicated coordinates systems. Thus, for example, the term ${}^{S}T_{N2}$ is a 6 DOF homogeneous transformation between the visible light coordinate system of the primary headset HMD1 1200 and the NIR coordinate system of the primary headset HMD1 1200.

In one embodiment, the XR headsets HMD1 1200 and HMD2 1210 have passive visible light markers painted or otherwise attached to them (coordinate systems S and A), such as the DRA fiducials 1310 shown in FIG. 13. The navigation cameras are spatially calibrated to these passive fiducials (coordinate systems N2 and N3).

As explained above, the cameras on the XR headset HMD1 1200 and HMD2 1210 and the navigation cameras 46 on the auxiliary tracking bar have partially overlapping field of views. If one or more of the cameras on the XR headset HMD1 1200 are obstructed from viewing a DRA attached to a tracked object, e.g., a tracked tool (T), but the DRA is in view of the cameras of the other XR headset HMD2 1210 and/or the navigation cameras 46 on the auxiliary tracking bar, the computer platform 910 can continue to track the DRA seamlessly without loss of navigation. Additionally, if there is partial occlusion of the DRA from the perspective of the cameras on the XR headset HMD1 1200, but the entire DRA is visible via cameras of the other XR headset HMD2 1210 and/or the navigation cameras 46 on the auxiliary tracking bar, the tracking inputs of the cameras can be merged to continue navigation of the DRA.

More particularly, the various coordinate systems can be chained together by virtue of independent observations the various camera systems provided by the XR headsets HMD1 1200 and HMD2 1210 and the navigation cameras 46 on the auxiliary tracking bar. For example, each of the XR headsets HMD1 1200 and HMD2 1210 may require virtual augmentation of the robotic end effector (E). While one XR headset HMD1 1200 (N2) and the navigation cameras 46 on the auxiliary tracking bar (N) are able to see (E), perhaps the other XR headset HMD2 1210 (N3) cannot. The location of (E) with respect to (N3) can still be computed via one of several different operational methods. Operations according to one embodiment performing chaining of poses from a patient reference (R). If the patient reference (R) is seen by (N3) and either one of (N) or (N2), the pose of (E) with respect to (N3) can be solved directly by either one of the following two equations:

$$T_{N3}^{E}=T_{N2}^{E}T_{R}^{N2}T_{N3}^{R}\text{—or—}T_{N3}^{E}=T_{N}^{E}T_{R}^{N}T_{N3}^{R}$$

They key to this pose chaining is that the relationship between the frames at the end of each chain are inferred (circled and transported below). The chains can be arbitrarily long and are enabled by having more than one stereo camera system (e.g., N, N2, N3).

Figure 21:
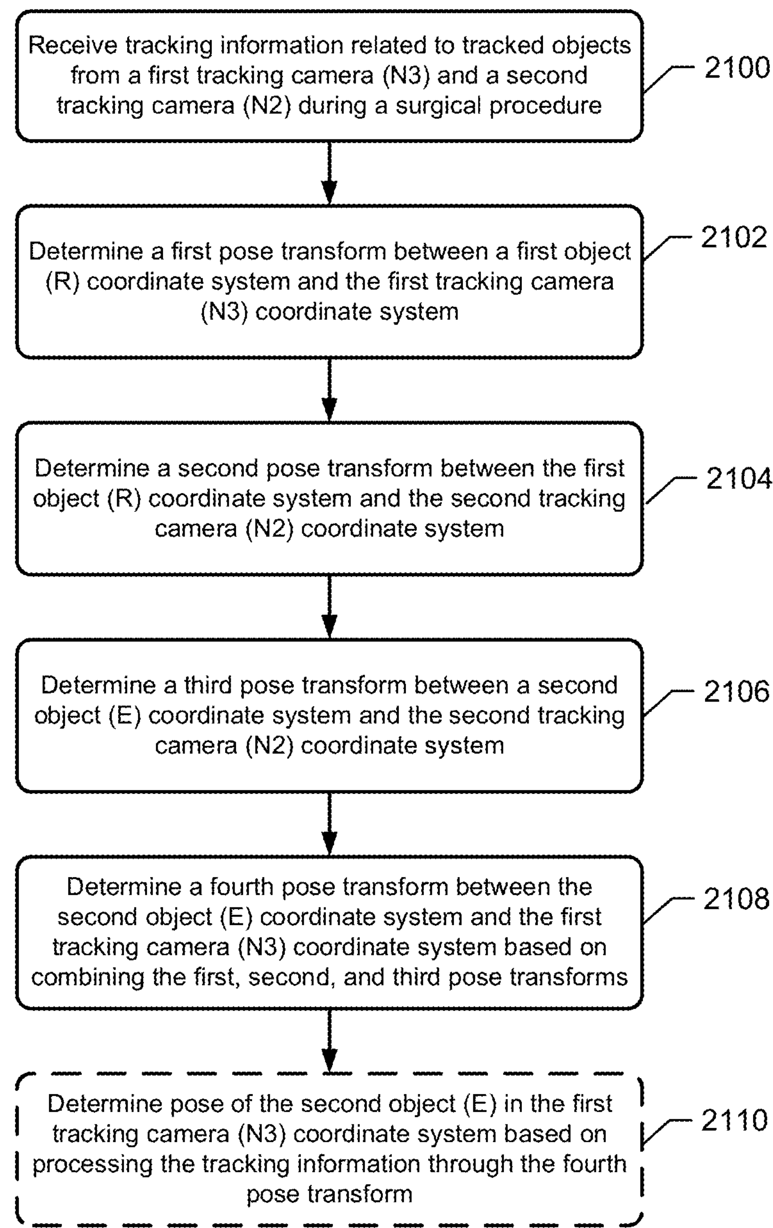
FIG. 21 is a flowchart of pose chaining operations that can be performed by a camera tracking system in accordance with some embodiments of the present disclosure.

FIG. 21 is a flowchart of corresponding operations that can be performed by a camera tracking system in accordance with some embodiments. Referring to FIG. 21, the camera tracking system can be configured to receive 2100 tracking information related to tracked objects from a first tracking camera (e.g., N3) and a second tracking camera (e.g., N2) during a surgical procedure. The camera tracking system can determine 2102 a first pose transform (e.g., $T_{N3}^{R}$) between a first object (e.g., R) coordinate system and the first tracking camera (e.g., N3) coordinate system based on first object tracking information from the first tracking camera (e.g., N3) which indicates pose of the first object (e.g., R). The camera tracking system can determine 2104 a second pose transform (e.g., $T_{R}^{N2}$) between the first object (e.g., R) coordinate system and the second tracking camera (e.g., N2) coordinate system based on first object tracking information from the second tracking camera (e.g., N2) which indicates pose of the first object (e.g., R). The camera tracking system can determine 2106 a third pose transform (e.g., $T_{N2}^{E}$) between a second object (e.g., E) coordinate system and the second tracking camera (e.g., N2) coordinate system based on second object tracking information from the second tracking camera (e.g., N2) which indicates pose of the second object (e.g., E). The camera tracking system can determine 2108 a fourth pose transform (e. g., $T_{N3}^{E}$) between the second object (e.g., E) coordinate system and the first tracking camera (e.g., N3) coordinate system based on combining the first, second, and third pose transforms.

In some further embodiments, the camera system can further determine 2110 pose of the second object (e.g., E) and the first tracking camera system (e.g., N3) coordinate system based on processing the tracking information through the fourth pose transform.

Because of the overlapping field of views of the various camera systems, the camera tracking system is capable of determining the pose of the second object (e.g., E) relative to first tracking camera (e.g., N3) when the first camera is blocked from seeing the second object (e.g., E). For example, in some embodiments the camera tracking system is further configured to determine the fourth pose transform (e. g., $T_{N3}^{E}$) between the second object (e.g., E) coordinate system and the first tracking camera (e.g., N3) coordinate system without use of any tracking information from the first tracking camera (e.g., N3) indicating pose of the second object (e.g., E).

The camera tracking system can be further configured to determine pose of the second object (e.g., E) in the first tracking camera (e.g., N3) coordinate system based on processing through the fourth pose transform the tracking information from the first tracking camera (e.g., N3) which indicates pose of the first object (e.g., R), based on processing through the fourth pose transform (e.g., $T_{N3}^{E}$) the tracking information from the second tracking camera (e.g., N2) which indicates pose of the first object (e.g., R), and based on processing through the fourth pose transform the tracking information from the second tracking camera (e.g., N2) which indicates pose of the second object (e.g., E).

The camera tracking system may achieve higher tracking accuracy by merging synchronized imagery from multiple camera systems. For example, the camera tracking system can determine pose of the second object (e.g., E) relative to first tracking camera (e.g., N3) by merging synchronized imagery of the second object (e.g., E) from multiple perspectives (first and second tracking cameras), and can use weighting which can be determined based on accuracy specs of the respective cameras. More particularly, the camera tracking system can be further configured to determine the fourth pose transform (e.g., $T_{N3}^{E}$) between the second object (e.g., E) coordinate system and the first tracking camera (e.g., N3) coordinate system based on second object tracking information from the first tracking camera (e.g., N3) which indicates pose of the second object (e.g., E) and further based on a result of the combining of the first, second, and third pose transforms.

The tracking system may be further configured to determine pose of the second object (e.g., E) based on applying a first weight to the first and second object tracking information from the first tracking camera (e.g., N3), applying a second weight to the first and second object tracking information from the second tracking camera (e.g., N2), and processing through the fourth pose transform (e. g., $T_{N3}^{E}$) the first weighted first and second object tracking information from the first tracking camera and the second weighted first and second object tracking information from the second tracking camera. The value of the first weight indicates pose determination accuracy of the first tracking camera (e.g., N3), and the value of the second weight indicates pose determination accuracy of the second tracking camera (e.g., N2).

The camera tracking system may be further configured to adapt the value of the first weight over time responsive to determined changes in pose determination accuracy of the first tracking camera (e.g., N3) during operation of the camera tracking system, and to adapt the value of the second weight over time responsive to determined changes in pose determination accuracy of the second tracking camera (e.g., N2) during operation of the camera tracking system.

The camera tracking system may be configured to: decrease the value of the first weight based on determining the pose determination accuracy of the first tracking camera (e.g., N3) has decreased; and increase the value of the first weight based on determining the pose determination accuracy of the first tracking camera (e.g., N3) has increased.

The camera tracking system may be further configured to adapt the value of at least one of the first and second weights over time responsive to determined changes in pose determination accuracy of the first tracking camera (e.g., N3) relative to pose determination accuracy of the second tracking camera (e.g., N2) during operation of the camera tracking system.

The surgical system may be configured to display on the see-through display screen of the XR headset an XR image having a pose that is determined based on the fourth pose transform. The camera tracking system may be further configured to generate the XR image as a graphical representation of the second object (e.g., E) that is posed on the see-through display screen based on processing through the fourth pose transform the first object tracking information from the first and second tracking cameras and the second object tracking information from the second tracking camera.

As explained above, the camera tracking system can include a navigation controller 828 communicatively connected to the first tracking camera (e.g., N3) and the second tracking camera (e.g., N2) to receive the tracking information and configured to perform the determination of the first, second, third, and fourth pose transforms.

Figure 19:
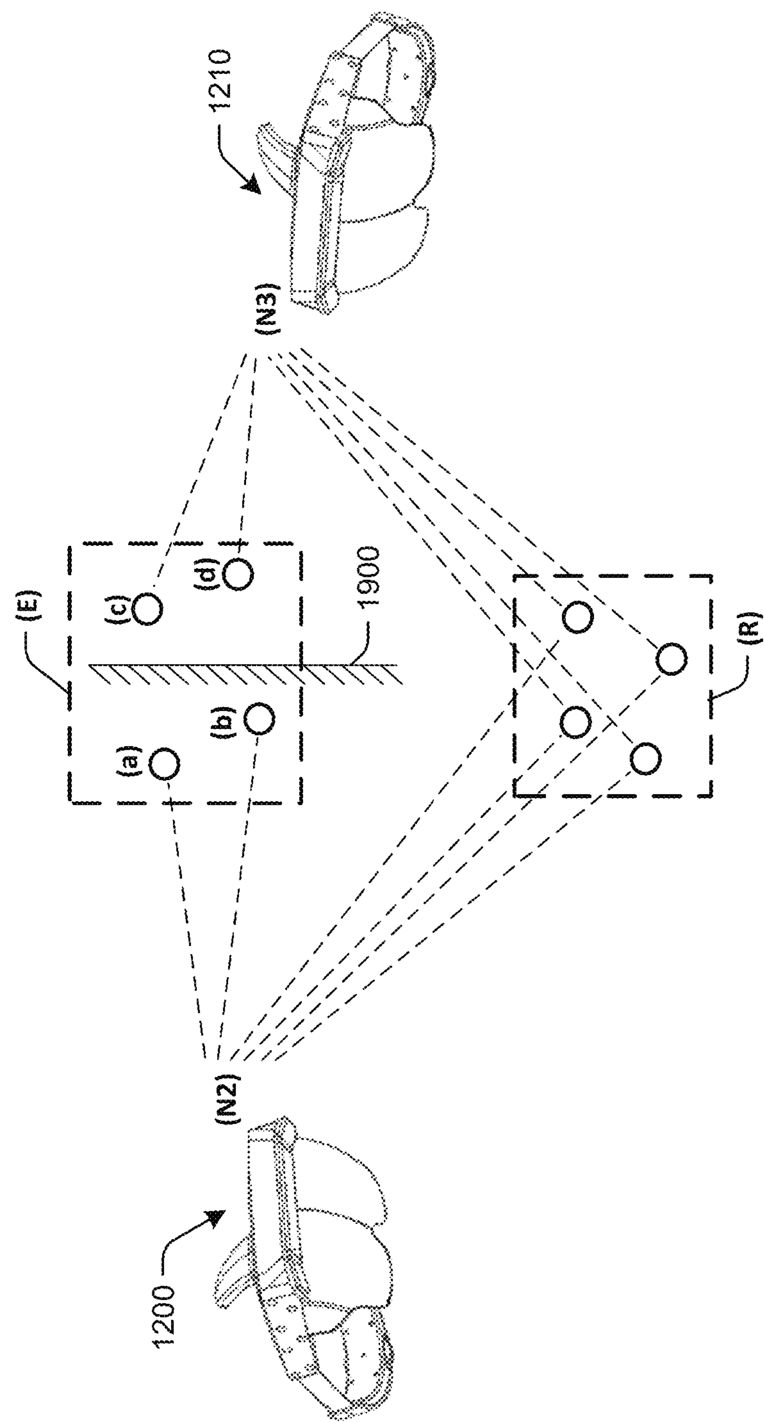
FIG. 19 illustrates a pair of XR headsets that operate with a camera tracking system to cooperatively tracking pose of dynamic reference array fiducials that cannot be fully directly observed by either XR headset, in accordance with some embodiments of the present disclosure.

FIG. 19 show another scenario in which an occlusion prevents cameras on both the XR headsets from directly seeing all of the DRA fiducials attached to the end effector (E), and related pose chaining operations that can be performed to fully resolve the pose of the end effector (E) relative to another tracked DRA (e.g., R). Even if a navigated instrument (e.g., T) or end effector (E) is not seen or recognized by any of the XR headsets' cameras, the navigated instrument (e.g., T) or end effector (E) can still be identified and localized by fusing location information obtained from tracking observable DRA fiducials from multiple perspectives relative to one joint coordinate system (e.g., R).

When an XR headset is not fully identifying any objects in near infrared or visible light, depending upon the camera configuration, but does see one or more stray DRA fiducials, the tracking light systems (V, S or A) can be used to know roughly where to expect to locate the one or more stray DRA fiducials their respective images. With this added tracking information, individual DRA fiducials can be identified and properly labeled inside of small regions of interest (ROI). The individual stray DRA fiducial information captured from different perspectives can then be combined and correlated in such a way that previously unidentifiable DRAs can now be identified.

Referring to the example scenario in FIG. 19, the XR headset 1200 (coordinate system N2) can observe all of the fiducials of the patient reference DRA (R) and can partially observe end effector (E) DRA fiducials (a) and (b) but cannot observe fiducials (c) and (d) because of an intervening occlusive surface 1900. The other XR headset 1210 (coordinate system N3) can also observe all of the fiducials of the patient reference DRA (R) and can partially observe end effector (E) DRA fiducials (c) and (d) but cannot observe fiducials (a) and (b) because of the intervening occlusive surface 1900.

Identifying and solving for the pose of the end effector (E) can be achieved from tracking cameras (N2) and (N3) by using (R) to chain the data into the same frame of reference. Even if neither headset camera system (N2) or (N3) perceive enough DRA fiducials to identify the end effector (E), the four individual DRA fiducials (a, b, c, d) that make up the end effector (E) are known relative to one another as well as the reference (R) due to pose chaining. What is needed for the end effector (E) to be usefully navigated in surgery is the relationship between the end effector (E) and the patient reference (R). That information can be independently computed as follows from either camera system:

$$T_R^{\,E}=T_{N2}^{\,E}T_R^{\,N2}\text{—or—}T_R^{\,E}=T_{N3}^{\,E}T_R^{\,N3}$$

The pose chaining determines $T_E^{\,N2}$ and $T_E^{\,N3}$. In order to detect and solve for the pose of the end effector (E) from the cameras (N2 and N3), the points (a, b, c, d) are put into the same coordinate system. The following translation vector operations can be performed for each stray DRA fiducial found. This provides each DRA fiducial relative to the same patient reference (R):

$$p_{aR}=p_{aN2}+p_{N2R}$$

$$p_{bR}=p_{bN2}+p_{N2R}$$

$$p_{cR}=p_{cN3}+p_{N3R}$$

$$p_{dR}=p_{dN3}+p_{N3R}$$

Once the location of all stray DRA fiducials relative to a patient reference are known ($p_{aR}$, $p_{bR}$, $p_{cR}$, $p_{dR}$), a conventional 3D "point to object" detection and pose recovery algorithm can be performed to determine the position and orientation of the robotic end effector (E) relative to the patient reference object (R). Operations of the detection and pose recovery algorithm can include: obtaining a predefined model of the pattern of the DRA fiducials including defined segment lengths between the fiducials; measuring the segments lengths between camera observed ones of the fiducials; and searching and comparing the observed relative segments lengths to pre-defined relative segments lengths from the predefined model of the pattern of the DRA fiducials.

Various corresponding operations that can be performed by the camera tracking system in accordance with some embodiments are explained below. As explained above, the DRAs can each include spaced apart fiducials which are attached to each of the first object (e.g., R), the second object (e.g., E), the first tracking camera (e.g., N3), and the second tracking camera (e.g., N2). The camera tracking system is further configured, while a first partially hidden fiducial (e.g., a) of the dynamic reference array attached to the second object (e.g., E) can be viewed by the second tracking camera (e.g., N2) but cannot be viewed by the first tracking camera (e.g., N3), to determine pose of the first partially hidden fiducial relative to the fiducials attached to the first object (e.g., R) based on a combination of a determined pose of the first partially hidden fiducial (e.g., a) relative to the fiducials attached to the second tracking camera (e.g., N2) and a determined pose of the fiducials attached to the second tracking camera (e.g., N2) relative to the fiducials attached to the first object (e.g., R).

The camera tracking system may be further configured, while a second partially hidden fiducial (e.g., b) of the dynamic reference array attached to the second object (e.g., E) can be viewed by the second tracking camera (e.g., N2) but cannot be viewed by the first tracking camera (e.g., N3), to determine pose of the second partially hidden fiducial (e.g., b) relative to the fiducials attached to the first object (e.g., R) based on a combination of a determined pose of the second partially hidden fiducial (e.g., b) relative to the fiducials attached to the second tracking camera (e.g., N2) and a determined pose of the fiducials attached to the second tracking camera (e.g., N2) relative to the fiducials attached to the first object (e.g., R).

The camera tracking system may be further configured, while a third partially hidden fiducial (e.g., c) of the dynamic reference array attached to the second object (e.g., E) cannot be viewed by the second tracking camera (e.g., N2) but can be viewed by the first tracking camera (e.g., N3), to determine pose of the third partially hidden fiducial (e.g., c) relative to the fiducials attached to the first object (e.g., R) based on a combination of a determined pose of the third partially hidden fiducial (e.g., c) relative to the fiducials attached to the first tracking camera (e.g., N3) and a determined pose of the fiducials attached to the first tracking camera (e.g., N3) relative to the fiducials attached to the first object (e.g., R).

The camera tracking system may be further configured to process the determined pose of the first partially hidden fiducial relative to the fiducials attached to the first object (e.g., R) and to process the determined pose of the third partially hidden fiducial (e.g., c) relative to the fiducials attached to the first object (e.g., R) through a pose recovery operation to determine pose of the second object (e.g., E) relative to the first object (e.g., R).

The camera tracking system may be further configured, while a fourth partially hidden fiducial (e.g., d) of the dynamic reference array attached to the second object (e.g., E) cannot be viewed by the second tracking camera (e.g., N2) but can be viewed by the first tracking camera (e.g., N3), to determine pose of the fourth partially hidden fiducial (e.g., d) relative to the fiducials attached to the first object (e.g., R) based on a combination of a determined pose of the fourth partially hidden fiducial (e.g., d) relative to the fiducials attached to the first tracking camera (e.g., N3) and a determined pose of the fiducials attached to the first tracking camera (e.g., N3) relative to the fiducials attached to the first object (e.g., R).

Potential advantages that may be provided by various embodiments disclosed herein may include any one or more of: tools that in some scenarios could not be previously tracked can now be robustly tracked by the sharing of partial obstructed views in the same coordinate system; accuracy of head and instrument tracking is improved by merging synchronized imagery from multiple perspectives; a much wider range of motion (position and orientation) is supported without losing tracking of instruments and robotic end effectors due to the expanded overall tracking volume; XR headsets can be tracked naturally in the same coordinate system as navigated instruments without any additional setup; and surgical safety and outcomes are improved due to the built-in tracking redundancy allowing for reliable identification of stereo cameras that are out of calibration or otherwise defective.

Figure 20:
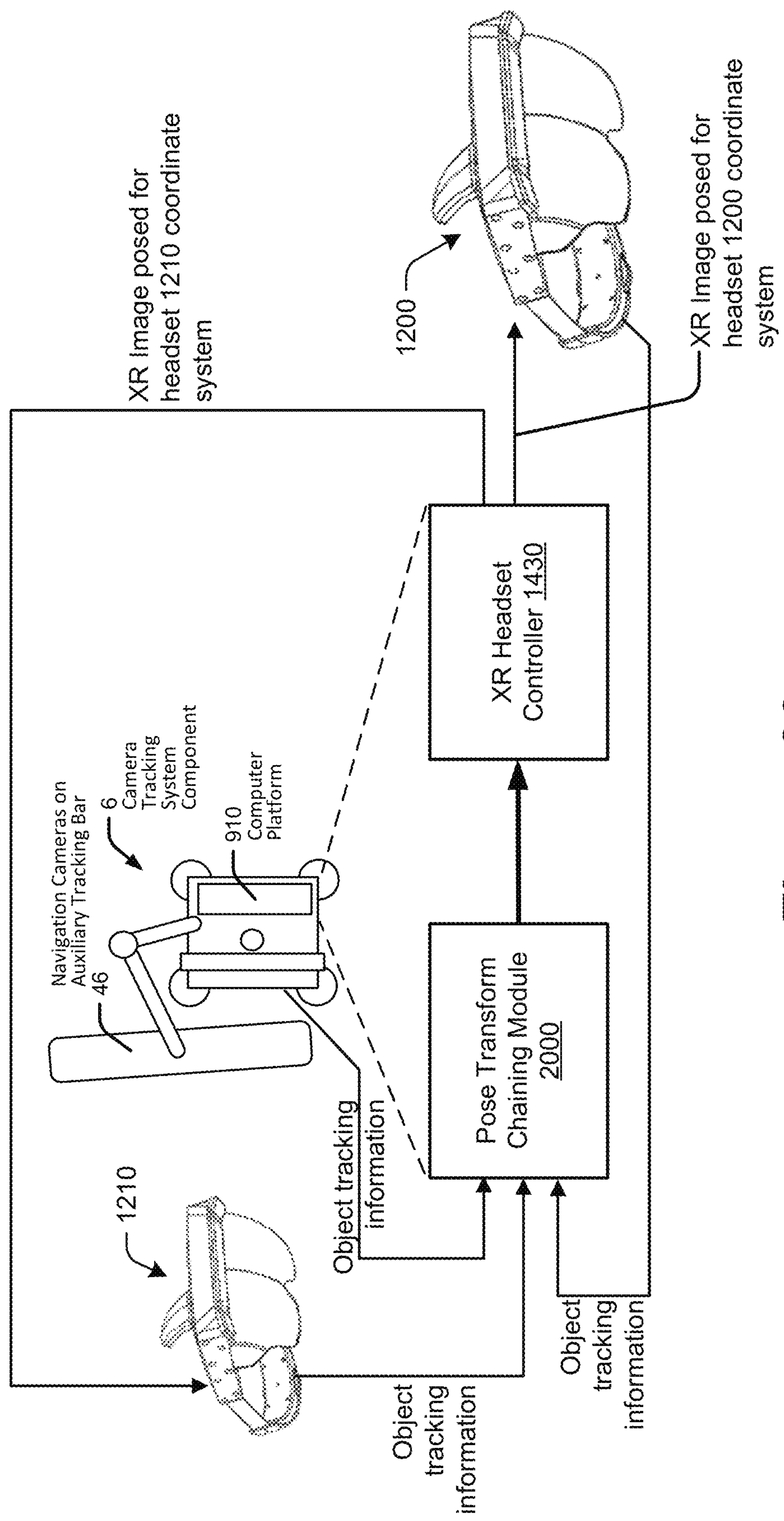
FIG. 20 illustrates a block diagram of information flows between various components of a surgical system operating in accordance with some embodiments of the present disclosure.

FIG. 20 illustrates a block diagram of information flows between various components of a surgical system operating in accordance with some embodiments of the present disclosure. Referring to FIG. 20, object tracking information flows from the XR headsets 1200 and 1200 to the pose transform chaining module 2000, and from the navigation cameras 46 on the auxiliary tracking bar to the pose transform chaining module 2000. The pose transform chaining module 2000 is configured to perform pose chaining in accordance with various embodiments explained above. The XR headset controller 1430 uses the object pose is determined by the pose transform chaining module 2000 to generate XR images that can be provided to the XR headsets 1200 and 1200 for display. The XR headset controller 1430 may generate the XR images for display on the XR headset 1200 based on present pose of the XR headset 1200, and similarly may generate the XR images for display on the XR headset 1210 based on present pose of the XR headset 1210. For example, as shown in FIG. 16 the XR headset 1200 can be provided a computer generated graphical representation 1600 of a tool 1602 that is scaled and posed for display on a see-through display screen so the user can accurately manipulate the tool 1602 while viewing the graphical representation 1600 relative to another graphical representation 1610 of an anatomical structure that is to be operated on using the tool during a surgical procedure.

Further Definitions and Embodiments:

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, micro-code, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Many variations and modifications can be made to the embodiments without substantially departing from the principles of the present inventive concepts. All such variations and modifications are intended to be included herein within the scope of present inventive concepts. Accordingly, the above disclosed subject matter is to be considered illustrative, and not restrictive, and the appended examples of embodiments are intended to cover all such modifications, enhancements, and other embodiments, which fall within the spirit and scope of present inventive concepts. Thus, to the maximum extent allowed by law, the scope of present inventive concepts are to be determined by the broadest permissible interpretation of the present disclosure including the following examples of embodiments and their equivalents, and shall not be restricted or limited by the foregoing detailed description.

What is claimed is:

1. A surgical system comprising:

a camera tracking system configured to receive tracking information related to tracked objects from a first tracking camera and a second tracking camera during a surgical procedure, determine a first pose transform between a first object coordinate system and the first tracking camera coordinate system based on first object tracking information from the first tracking camera which indicates pose of the first object, determine a second pose transform between the first object coordinate system and the second tracking camera coordinate system based on first object tracking information from the second tracking camera which indicates pose of the first object, determine a third pose transform between a second object coordinate system and the second tracking camera coordinate system based on second object tracking information from the second tracking camera which indicates pose of the second object, and determine a fourth pose transform between the second object coordinate system and the first tracking camera coordinate system based on combining the first, second, and third pose transforms.

2. The surgical system of claim 1, wherein the camera tracking system is further configured to determine the fourth pose transform between the second object coordinate system and the first tracking camera coordinate system without use of any tracking information from the first tracking camera indicating pose of the second object.

3. The surgical system of claim 1, wherein the camera tracking system is further configured to determine pose of the second object in the first tracking camera coordinate system based on processing through the fourth pose transform the tracking information from the first tracking camera which indicates pose of the first object, based on processing through the fourth pose transform the tracking information from the second tracking camera which indicates pose of the first object, and based on processing through the fourth pose transform the tracking information from the second tracking camera which indicates pose of the second object.

4. The surgical system of claim 1, wherein the camera tracking system is further configured to determine the fourth pose transform between the second object coordinate system and the first tracking camera coordinate system based on second object tracking information from the first tracking camera which indicates pose of the second object and further based on a result of the combining of the first, second, and third pose transforms.

5. The surgical system of claim 4, wherein the camera tracking system is further configured to determine pose of the second object based on applying a first weight to the first and second object tracking information from the first tracking camera, applying a second weight to the first and second object tracking information from the second tracking camera, and processing through the fourth pose transform the first weighted first and second object tracking information from the first tracking camera and the second weighted first and second object tracking information from the second tracking camera, wherein a value of the first weight indicates pose determination accuracy of the first tracking camera, wherein a value of the second weight indicates pose determination accuracy of the second tracking camera.

6. The surgical system of claim 5, wherein the camera tracking system is further configured to adapt the value of the first weight over time responsive to determined changes in pose determination accuracy of the first tracking camera during operation of the camera tracking system, and to adapt the value of the second weight over time responsive to determined changes in pose determination accuracy of the second tracking camera during operation of the camera tracking system.

7. The surgical system of claim 6, wherein the camera tracking system is configured to:

decrease the value of the first weight based on determining the pose determination accuracy of the first tracking camera has decreased; and increase the value of the first weight based on determining the pose determination accuracy of the first tracking camera has increased.

8. The surgical system of claim 5, wherein the camera tracking system is further configured to adapt the value of at least one of the first and second weights over time responsive to determined changes in pose determination accuracy of the first tracking camera relative to pose determination accuracy of the second tracking camera during operation of the camera tracking system.

9. The surgical system of claim 1, further comprising an extended reality (XR) headset including the first tracking camera and a see-through display screen, the XR headset being configured to be worn by a user during the surgical procedure, the camera tracking system is further configured to:

display on the see-through display screen of the XR headset an XR image having a pose that is determined based on the fourth pose transform.

10. The surgical system of claim 9, wherein the camera tracking system is further configured to:

generate the XR image as a graphical representation of the second object that is posed on the see-through display screen based on processing through the fourth pose transform the first object tracking information from the first and second tracking cameras and the second object tracking information from the second tracking camera.

11. The surgical system of claim 9, wherein the camera tracking system comprises a navigation controller communicatively connected to the first and second tracking cameras to receive the tracking information and configured to perform the determination of the first, second, third, and fourth pose transforms.

12. The surgical system of claim 1, wherein:

dynamic reference arrays including spaced apart fiducials are attached to each of the first object, the second object, the first tracking camera, and the second tracking camera; and the camera tracking system is further configured, while a first partially hidden fiducial of the dynamic reference array attached to the second object can be viewed by the second tracking camera but cannot be viewed by the first tracking camera, to determine pose of the first partially hidden fiducial relative to the fiducials attached to the first object based on a combination of a determined pose of the first partially hidden fiducial relative to the fiducials attached to the second tracking camera and a determined pose of the fiducials attached to the second tracking camera relative to the fiducials attached to the first object.

13. The surgical system of claim 12, wherein:

the camera tracking system is further configured, while a second partially hidden fiducial of the dynamic reference array attached to the second object can be viewed by the second tracking camera but cannot be viewed by the first tracking camera, to determine pose of the second partially hidden fiducial relative to the fiducials attached to the first object based on a combination of a determined pose of the second partially hidden fiducial relative to the fiducials attached to the second tracking camera and a determined pose of the fiducials attached to the second tracking camera relative to the fiducials attached to the first object.

14. The surgical system of claim 12, wherein:

the camera tracking system is further configured, while a third partially hidden fiducial of the dynamic reference array attached to the second object cannot be viewed by the second tracking camera but can be viewed by the first tracking camera, to determine pose of the third partially hidden fiducial relative to the fiducials attached to the first object based on a combination of a determined pose of the third partially hidden fiducial relative to the fiducials attached to the first tracking camera and a determined pose of the fiducials attached to the first tracking camera relative to the fiducials attached to the first object.

15. The surgical system of claim 14, wherein the camera tracking system is further configured to process the determined pose of the first partially hidden fiducial relative to the fiducials attached to the first object and to process the determined pose of the third partially hidden fiducial relative to the fiducials attached to the first object through a pose recovery operation to determine pose of the second object relative to the first object.

16. The surgical system of claim 14, wherein:

the camera tracking system is further configured, while a fourth partially hidden fiducial of the dynamic reference array attached to the second object cannot be viewed by the second tracking camera but can be viewed by the first tracking camera, to determine pose of the fourth partially hidden fiducial relative to the fiducials attached to the first object based on a combination of a determined pose of the fourth partially hidden fiducial relative to the fiducials attached to the first tracking camera and a determined pose of the fiducials attached to the first tracking camera relative to the fiducials attached to the first object.

17. A method by a camera tracking system comprising:

receiving tracking information related to tracked objects from a first tracking camera and a second tracking camera during a surgical procedure, determining a first pose transform between a first object coordinate system and the first tracking camera coordinate system based on first object tracking information from the first tracking camera which indicates pose of the first object, determining a second pose transform between the first object coordinate system and the second tracking camera coordinate system based on first object tracking information from the second tracking camera which indicates pose of the first object, determining a third pose transform between a second object coordinate system and the second tracking camera coordinate system based on second object tracking information from the second tracking camera which indicates pose of the second object, and determining a fourth pose transform between the second object coordinate system and the first tracking camera coordinate system based on combining the first, second, and third pose transforms.

18. The method of claim 17, further comprising determining pose of the second object in the first tracking camera coordinate system based on processing through the fourth pose transform the tracking information from the first tracking camera which indicates pose of the first object, based on processing through the fourth pose transform the tracking information from the second tracking camera which indicates pose of the first object, and based on processing through the fourth pose transform the tracking information from the second tracking camera which indicates pose of the second object.

19. A computer program product comprising:

a non-transitory computer readable medium storing program code executable by at least one processor of a camera tracking system to receive tracking information related to tracked objects from a first tracking camera and a second tracking camera during a surgical procedure, determine a first pose transform between a first object coordinate system and the first tracking camera coordinate system based on first object tracking information from the first tracking camera which indicates pose of the first object, determine a second pose transform between the first object coordinate system and the second tracking camera coordinate system based on first object tracking information from the second tracking camera which indicates pose of the first object, determine a third pose transform between a second object coordinate system and the second tracking camera coordinate system based on second object tracking information from the second tracking camera which indicates pose of the second object, and determine a fourth pose transform between the second object coordinate system and the first tracking camera coordinate system based on combining the first, second, and third pose transforms.

20. The computer program product of claim 19, wherein the program code is further executable by the at least one processor of the camera tracking system to determine pose of the second object in the first tracking camera coordinate system based on processing through the fourth pose transform the tracking information from the first tracking camera which indicates pose of the first object, based on processing through the fourth pose transform the tracking information from the second tracking camera which indicates pose of the first object, and based on processing through the fourth pose transform the tracking information from the second tracking camera which indicates pose of the second object.

* * * * *